United States Patent [19]

Sprecker et al.

[11] Patent Number: 4,608,193
[45] Date of Patent: Aug. 26, 1986

[54] ISOCHROMAN DERIVATIVES AND ORGANOLEPTIC USES THEREOF

[75] Inventors: Mark A. Sprecker, Sea Bright; Wilhelmus J. Wiegers, Red Bank; Roger Greene, Oakhurst; Domenick Luccarelli, Jr., Neptune; Marie Hanna, Hazlet, all of N.J.

[73] Assignee: International Flavors & Fragrances Inc., New York, N.Y.

[21] Appl. No.: 765,212

[22] Filed: Aug. 13, 1985

Related U.S. Application Data

[60] Continuation of Ser. No. 551,552, Nov. 14, 1983, which is a division of Ser. No. 430,951, Sep. 30, 1982, abandoned.

[51] Int. Cl.$^4$ .............................................. A61K 7/46
[52] U.S. Cl. .................................................. 252/522 R
[58] Field of Search ..................... 252/522 R; 549/385

[56] References Cited

U.S. PATENT DOCUMENTS

| | | | |
|---|---|---|---|
| 3,978,090 | 8/1976 | Sanders et al. | 549/385 |
| 4,162,256 | 7/1979 | Sprecker et al. | 252/522 R X |
| 4,250,200 | 2/1981 | Wiegers et al. | 252/522 R X |
| 4,265,818 | 5/1981 | Wiegers et al. | 549/385 |

OTHER PUBLICATIONS

Beets, "Parfumerie/Les Muscs/Scteur et Odeur", La France et ses Parfume 10 (1953), 1957.

*Primary Examiner*—Anton H. Sutto
*Attorney, Agent, or Firm*—Arthur L. Liberman

[57] ABSTRACT

Processes and compositions are described for the use in foodstuff flavor and aroma and perfumes and perfumed articles aroma augmenting, modifying, altering and enhancing compositions and as foodstuff, chewing gum, toothpaste, medicinal product, perfumes and perfumed articles aroma imparting materials of tricyclic isochroman mixtures wherein in the mixtures each of the compounds is defined according to the structure:

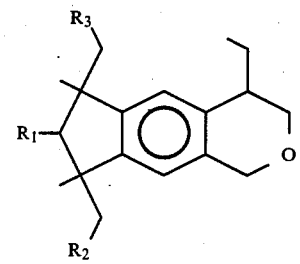

wherein $R_1$, $R_2$ and $R_3$ represent methyl or hydrogen with the proviso that when one of $R_1$, $R_2$ and $R_3$ is methyl, the other of $R_1$, $R_2$ and $R_3$ represents hydrogen.

Addition of said tricyclic isochroman mixtures is indicated to produce:
a. In food flavorings a sweet, musky aroma and taste; and
b. In perfumes and perfumed articles and colognes a sweet, musk aroma.

2 Claims, 7 Drawing Figures

GLC PROFILE FOR FRACTION 8 OF EXAMPLE I.

NMR SPECTRUM FOR EXAMPLE I.

GLC PROFILE FOR EXAMPLE II.
CRUDE

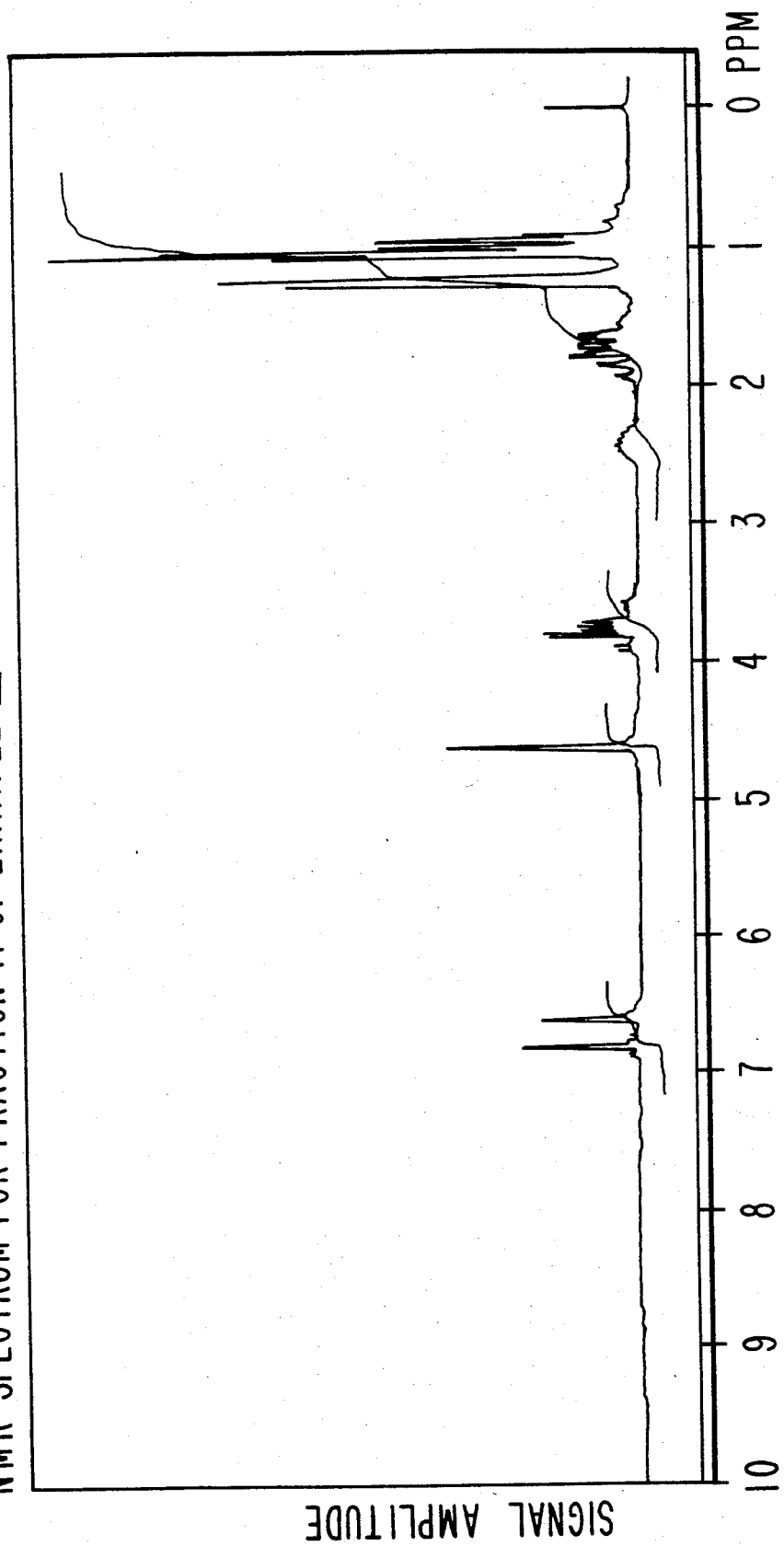

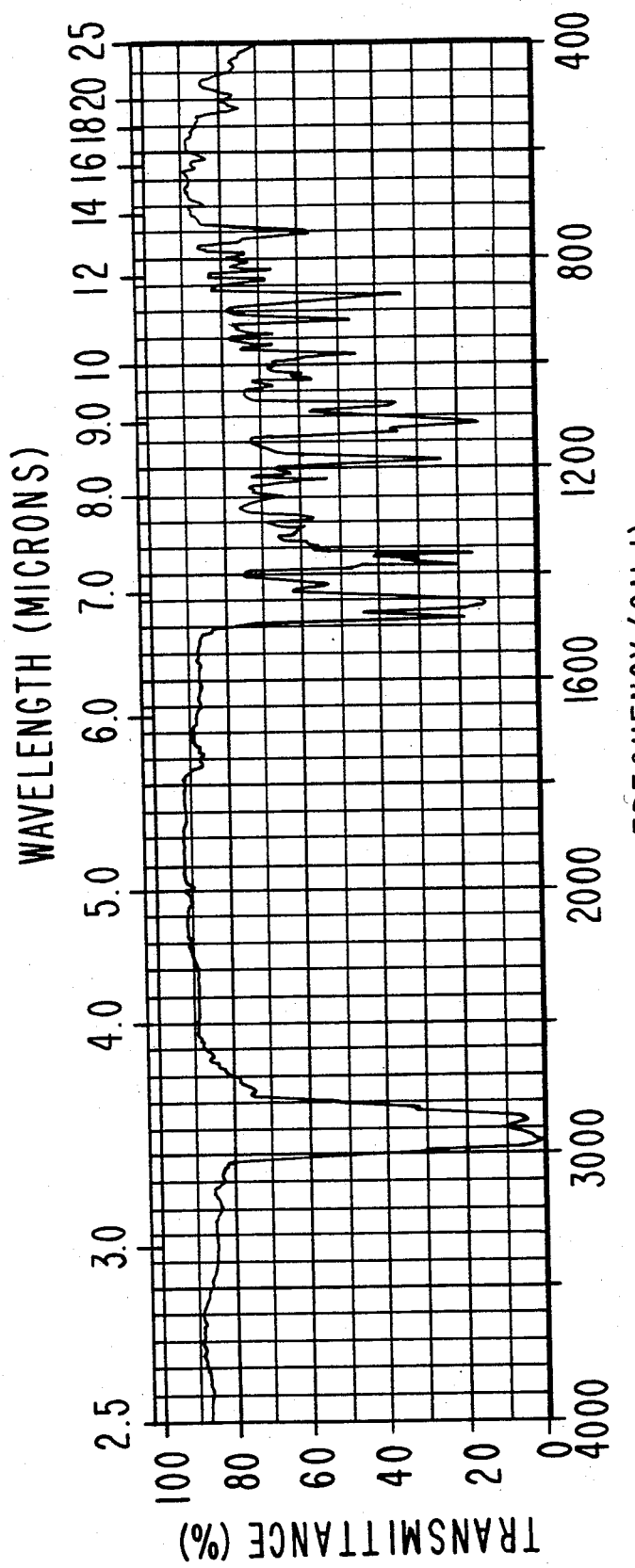

ISOCHROMAN DERIVATIVES AND ORGANOLEPTIC USES THEREOF

This is a continuation of application Ser. No. 551,552, filed Nov. 14, 1983, which, in turn, is a divisional of application for U.S. Letters Patent, Ser. No. 430,951, filed Sept. 30, 1982, now abandoned.

BACKGROUND OF THE INVENTION

The present invention relates to mixtures of ethyl substituted tricyclic isochromans defined according to the structure:

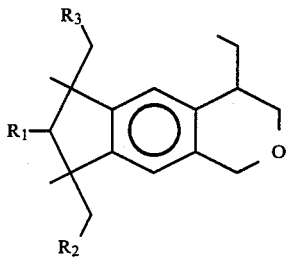

wherein $R_1$, $R_2$ and $R_3$ represent methyl or hydrogen with the proviso that when one of $R_1$, $R_2$ and $R_3$ is methyl, the other of $R_1$, $R_2$ and $R_3$ represents hydrogen; and organoleptic uses thereof as well as intermediates for producing said compounds defined according to the structure:

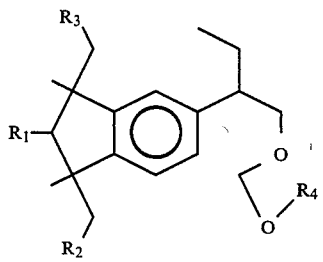

wherein $R_1$, $R_2$ and $R_3$ are defined, supra; and wherein $R_4$ represents $C_1$–$C_6$ lower alkyl and according to the structure:

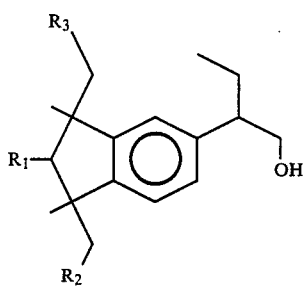

wherein $R_1$, $R_2$ and $R_3$ are defined, supra.

There has been considerable work performed relating to substances which can be used to impart (or alter, modify or enhance) flavors and fragrances to (or in) various consumable materials. These substances are used to diminish the use of natural materials, some of which may be in short supply and to provide more uniform properties in the finished product. Sweet and musky aroma characteristics and sweet and musky flavor characteristics are particularly desirable for many uses in foodstuff flavors, particularly pear, apricot and peach flavors. Musky aromas are desirable in several types of perfume compositions and for use in perfumed articles.

The production of isochromans has been shown in the prior art and certain novel isochromans have recently been disclosed with an outstanding musk fragrance. Such isochromans especially adapted for perfumery by virtue of their fragrance properties have been disclosed in Heeringa and Beets, U.S. Pat. No. 3,360,530 issued on Dec. 26, 1967.

A number of routes have been shown to be available for the production of isochromans, such as those set forth in U.S. Pat. No. 3,360,530 and one of the most straight forward of these routes in treatment of a Friedel Crafts reactant with an alkylene oxide under Friedel Crafts conditions to form an aryl alkanol. The aryl alkanol is then isolated and thereafter reacted with formaldehyde to cyclialkylate the alcohol.

In addition, several other references set forth processes for the production of isochromans such as U.S. Pat. No. 3,532,719 and U.S. Pat. No. 3,910,964 as well as U.S. Pat. No. 3,978,090.

The aforementioned references set forth production of compounds having the structure:

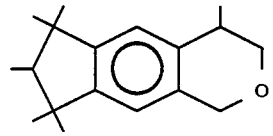

using as a precursor pentamethyl indane having the structure:

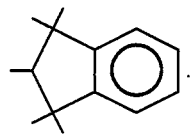

U.S. Pat. No. 4,265,818 sets forth production of compounds defined according to the structures:

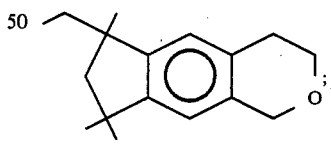

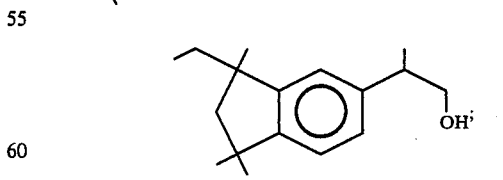

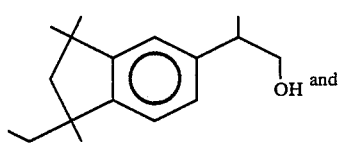

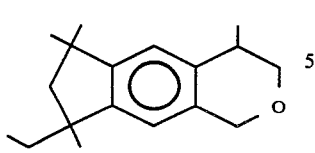

using as a precursor the tetraalkyl indane having the structure:

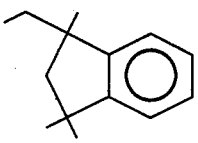

More specifically, U.S. Pat. No. 4,265,818 discloses a product consisting essentially of compounds having the structures:

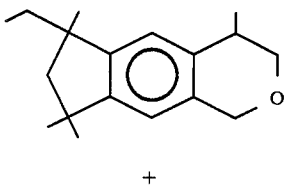

+

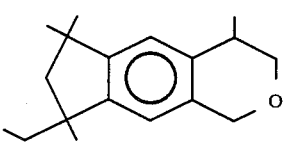

+

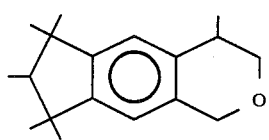

produced according to the process comprising the steps of (i) reacting isoamylene with alpha methyl styrene according to the reaction:

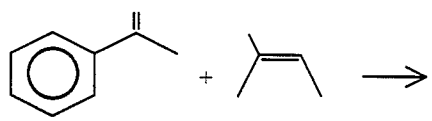

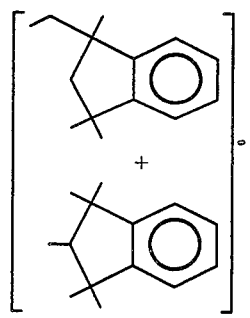

in the presence of a heterogeneous solid catalyst selected from the group consisting of acid clays and acid ion exchange resins, the mole ratio of isoamylene to alpha methyl styrene being between 1:1 and 2:1; the ratio of catalyst to reactants being from 0.1% up to 8% of the total weight of alpha methyl styrene and isoamylene; the reaction temperature being between 75° C. and 250° C.; the reaction pressure being between 50 psig and 300 psig; (ii) reacting the resulting product with propylene oxide in the presence of a catalyst to produce a mixture consisting essentially of indane alkanols according to the reaction:

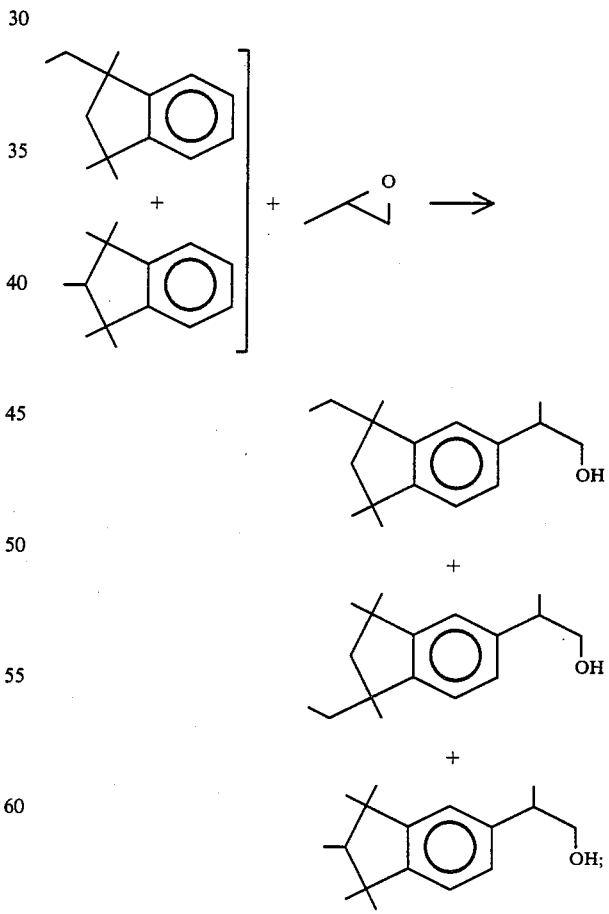

and (iii) reacting the mixture consisting essentially of indane alkanols with a formaldehyde or a formaldehyde source according to the reaction:

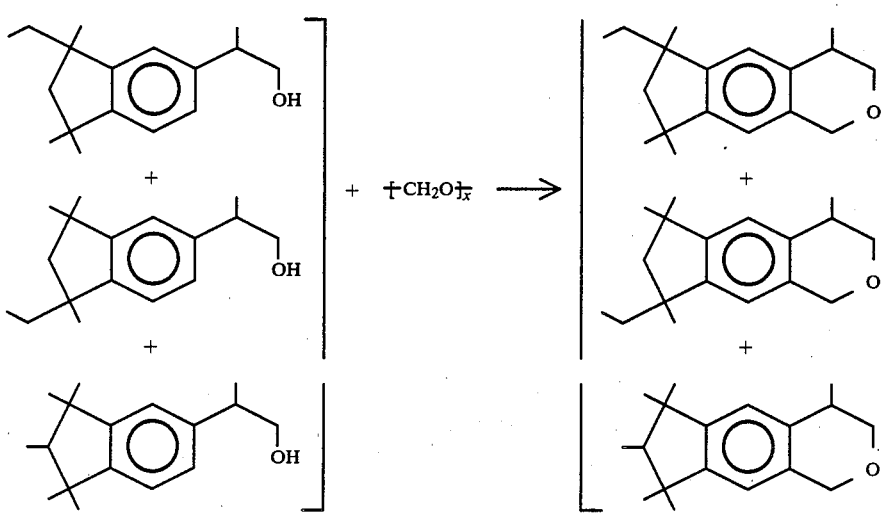

The said U.S. Pat. No. 4,265,818 also indicates the use of the compounds and mixtures so produced for augmenting or enhancing food flavors and fragrances. Specifically, the compounds of U.S. Pat. No. 4,265,818 indicate the usefulness of the compounds and mixtures produced for augmenting or enhancing musky aromas and pear, apricot and peach flavors.

U.S. Pat. No. 4,250,200 issued on Feb. 10, 1981 discloses and claims a process for augmenting or enhancing the pear aroma or taste of the pear flavor foodstuff comprising the step of adding to said foodstuff a flavor aroma augmenting or enhancing quantity of a mixture of compounds having the structures:

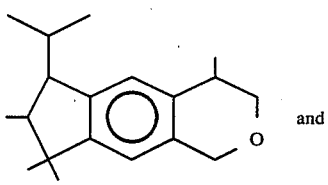 and

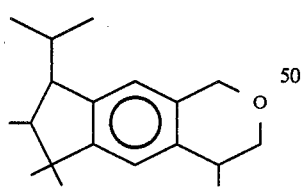

U.S. Pat. No. 3,978,090 issued on Aug. 31, 1976 discloses and claims processes for producing compounds defined according to the structure:

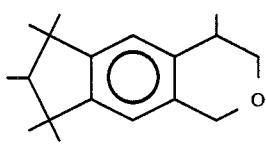

as well as compounds defined according to the generic structure:

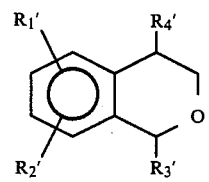

wherein $R_1'$ and $R_2'$ are each (i) separately selected from the group consisting of hydrogen, lower alkoxyl or lower alkyl, and (ii) taken together, as selected from the group consisting of benzo, cyclopentano, cyclohexano, naphtho, monoalkyl cyclopentano, polyalkyl cyclopentano, monoalkyl cyclohexano and polyalkyl cyclohexano, and $R_3'$ and $R_4'$ are the same or different and are selected from the group consisting of hydrogen and lower alkyl. The compounds defined according to the structure:

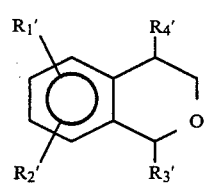

are indicated to be produced according to the reaction:

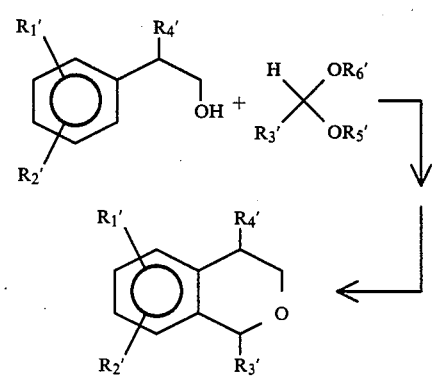

wherein $R_5'$ and $R_6'$ are each 2-propyl. Indicated as a starting material at column 5, line 22 of U.S. Pat. No. 3,978,090 is the compound defined according to the structure:

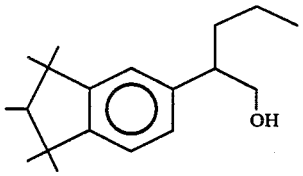

Ethyl substituted tricyclic isochroman compounds having musk aromas are also disclosed in Beets, "PARFUMERIE/LES MUSCS/Scteur et Odeur", La France et ses Parfums 10 (1953), 1957 wherein the compound having the structure:

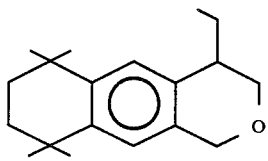

is disclosed as having a musk aroma.

Nothing in the prior art however, discloses the existence of the ethyl substituted tricyclic isochromans defined according to the structures:

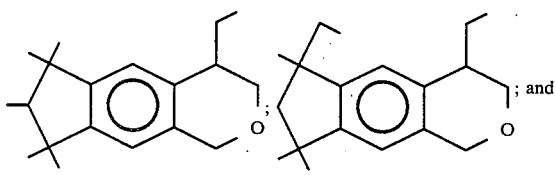

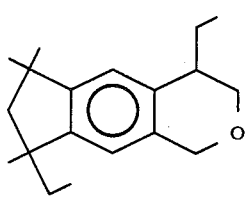

or intermediates for preparing same having the structures:

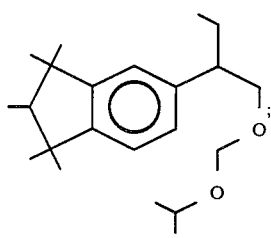

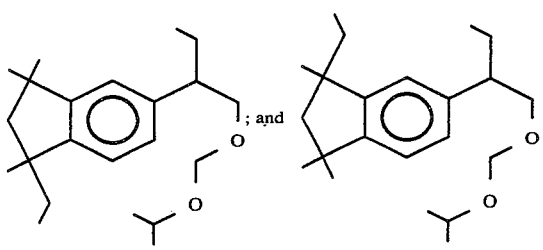

or:

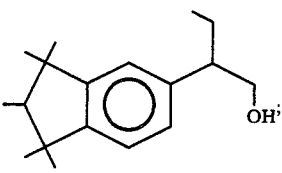

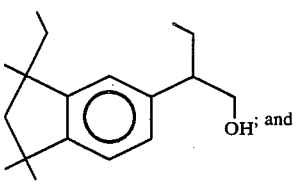 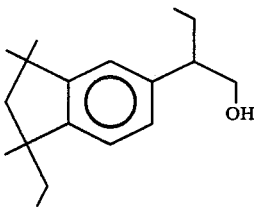

or:

and nothing in the prior art discloses the unexpected, unobvious and advantageous organoleptic properties of the compounds defined according to the structures:

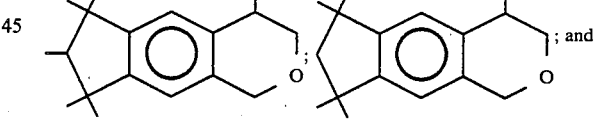

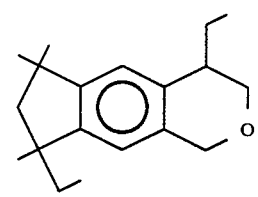

or mixtures of same.

BRIEF DESCRIPTION OF THE DRAWINGS

FIG. A is the GLC profile for the filtered reaction mixture prior to distillation produced according to Example A-1 containing the polyalkyl indanes defined according to the structures.

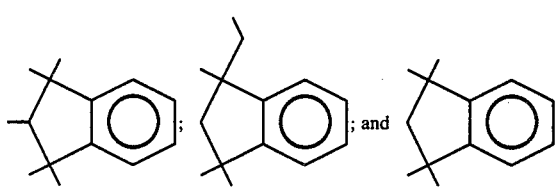 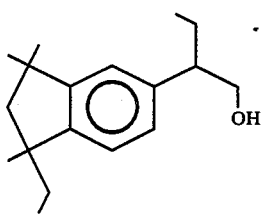

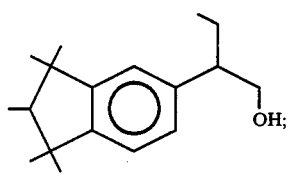

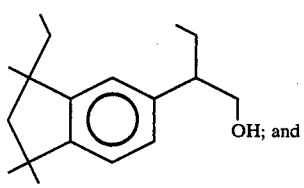

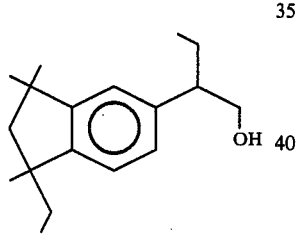

Figure 2:
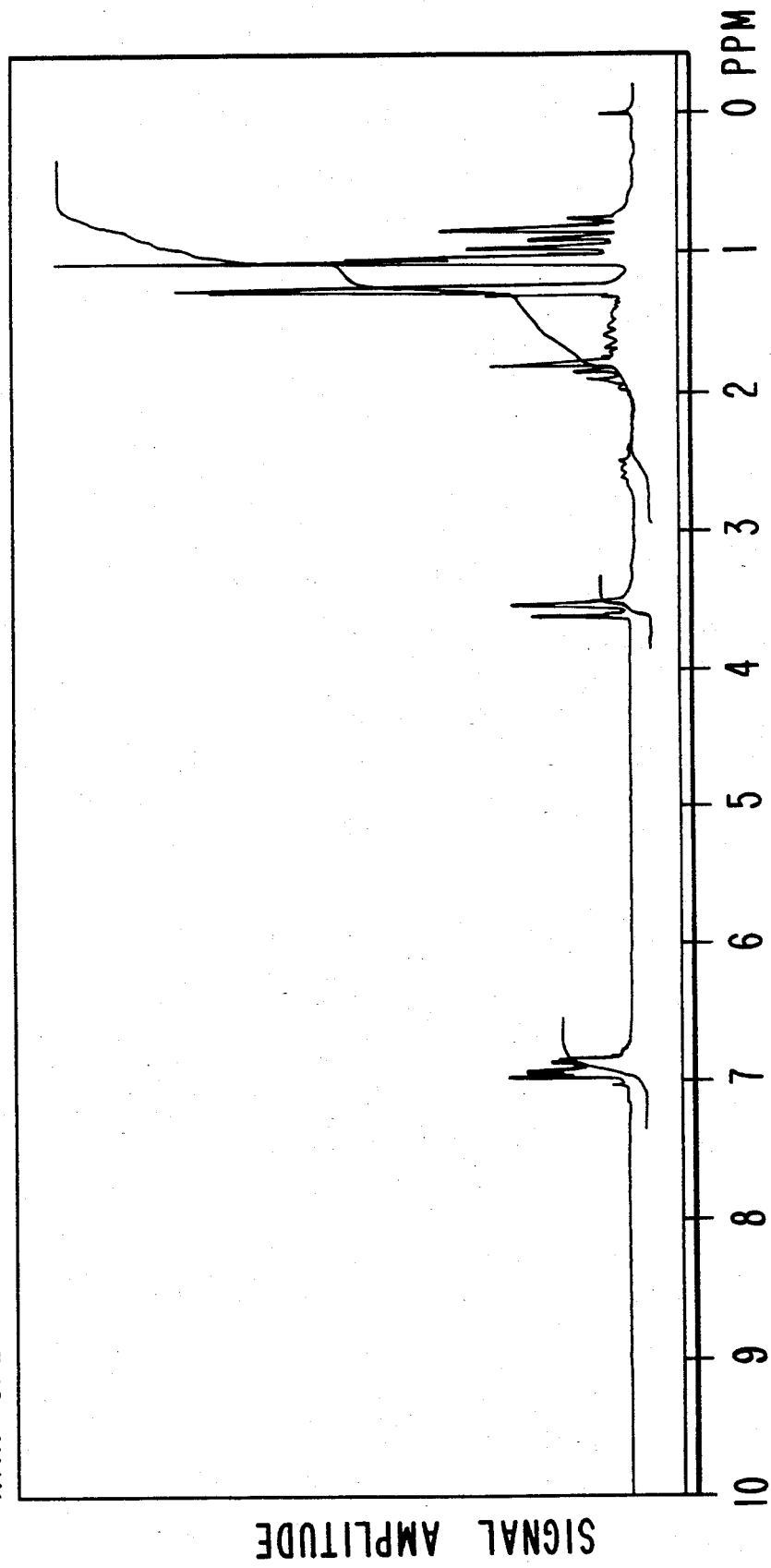

FIG. 2 is the NMR spectrum for the reaction product of Example I containing the compounds having the structures:

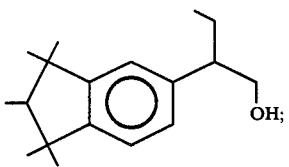

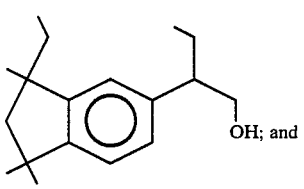

(solvent: CFCl₃; field strength 100 MH$_z$).

Figure 3:
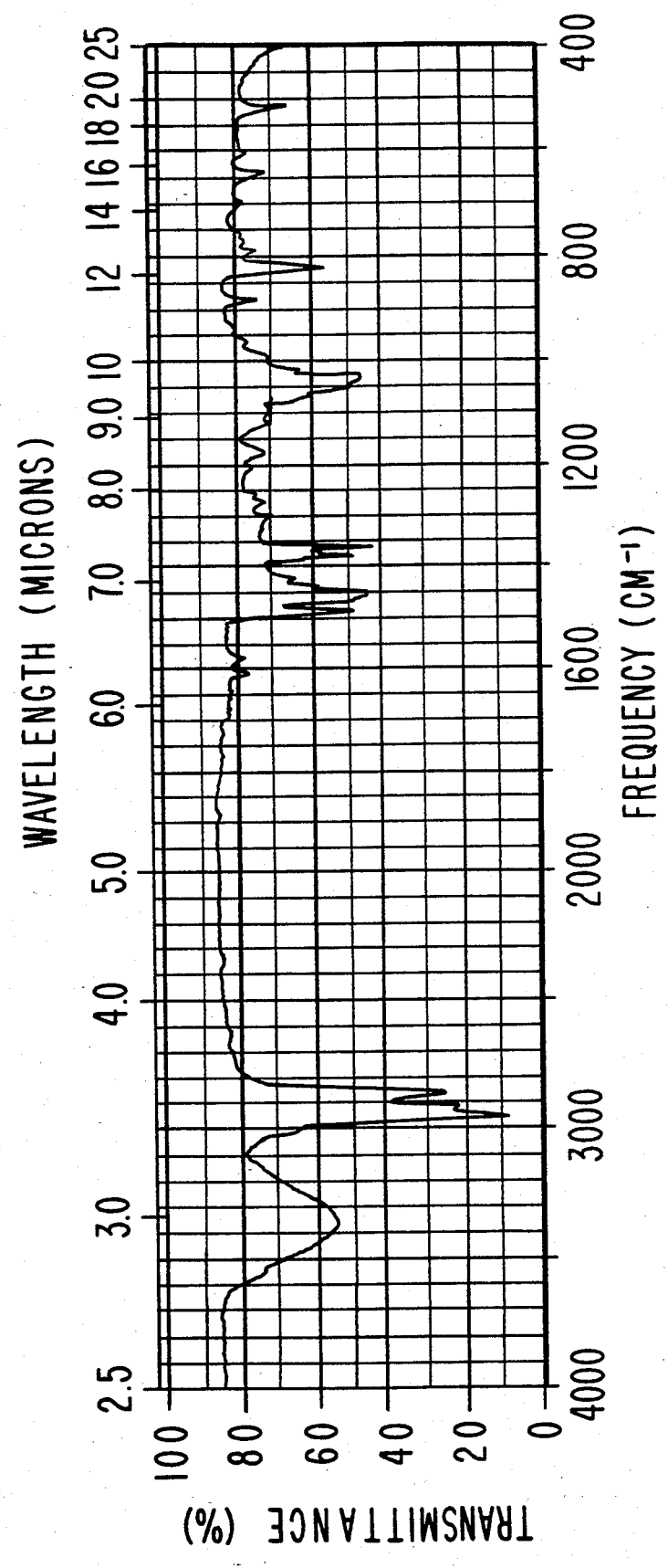

FIG. 3 is the infra-red spectrum for the reaction product of Example I containing the compounds having the structures:

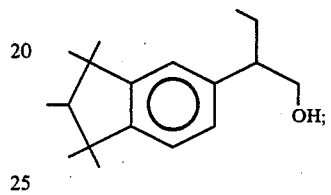

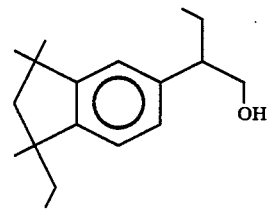

Figure 4:
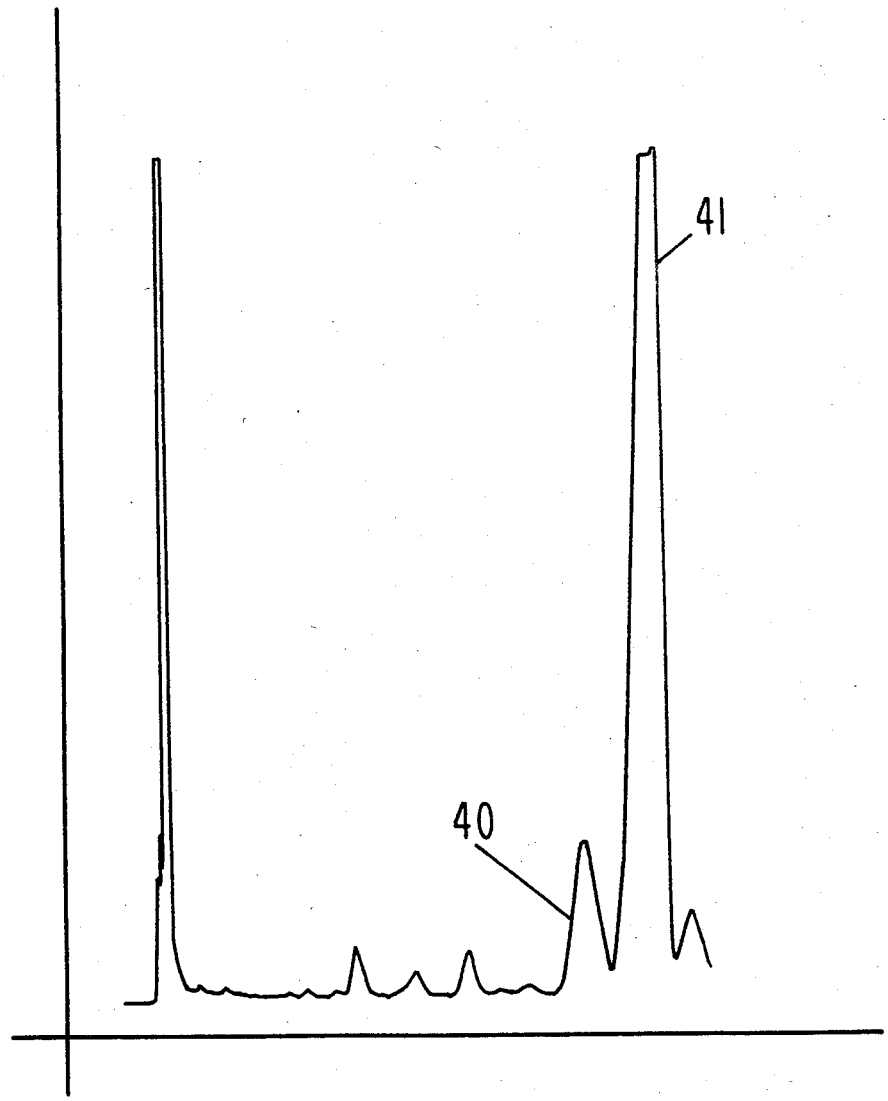

FIG. 4 is the GLC profile for the crude reaction product of Example II, prior to distillation containing the compounds having the structures:

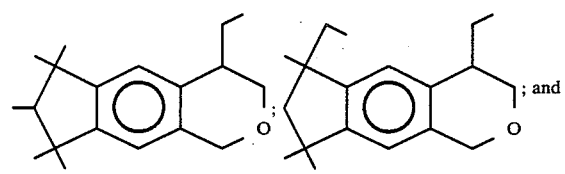

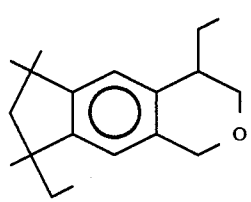

FIG. 5 is the NMR spectrum for Fraction 11 of the distillation product of the reaction product of Example II containing the compounds having the structures:

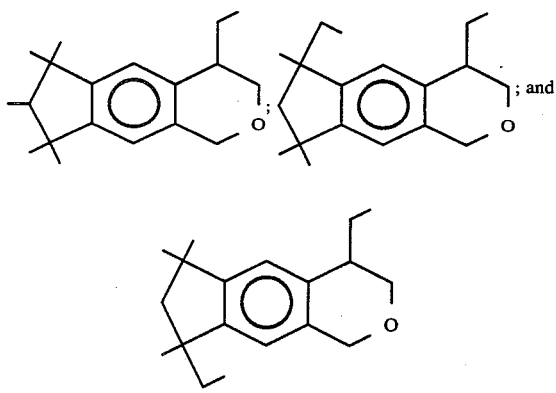

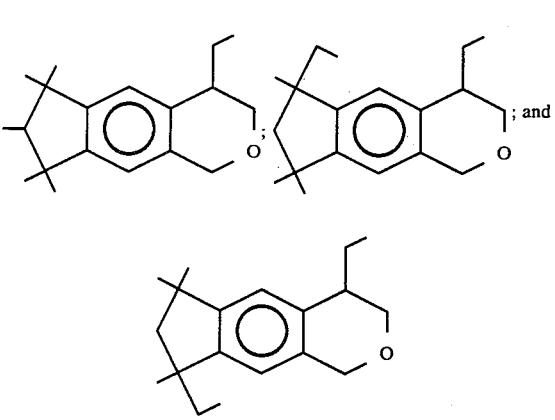

(Solvent: CFCl₃; field strength 100 MH₂).

FIG. 6 is the infra-red spectrum for Fraction 11 of the distillation product of the reaction product of Example II containing the compounds having the structures:

DETAILED DESCRIPTION OF THE DRAWINGS

Figure A is the GLC profile for the reaction product of Example A-1 (filtered reaction mixture prior to distillation). Conditions: 5% carbowax column, 10'×¼''', programmed at 125° C. isothermal. In Figure A, the peak indicated by reference numeral "1" is the peak for the compound having the structure:

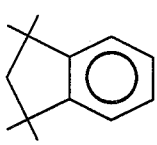

The peak indicated by reference numeral "2" is the peak for the compound having the structure:

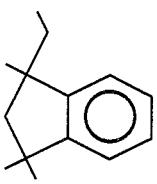

The peak indicated by reference numeral "3" is the peak for the compound having the structure:

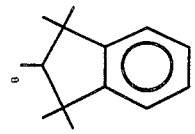

The peaks indicated by the reference numeral "4" are peaks for dimers of amylene. The peak indicated by reference numeral "5" is the peak for alpha methyl styrene dimer.

Figure 1:
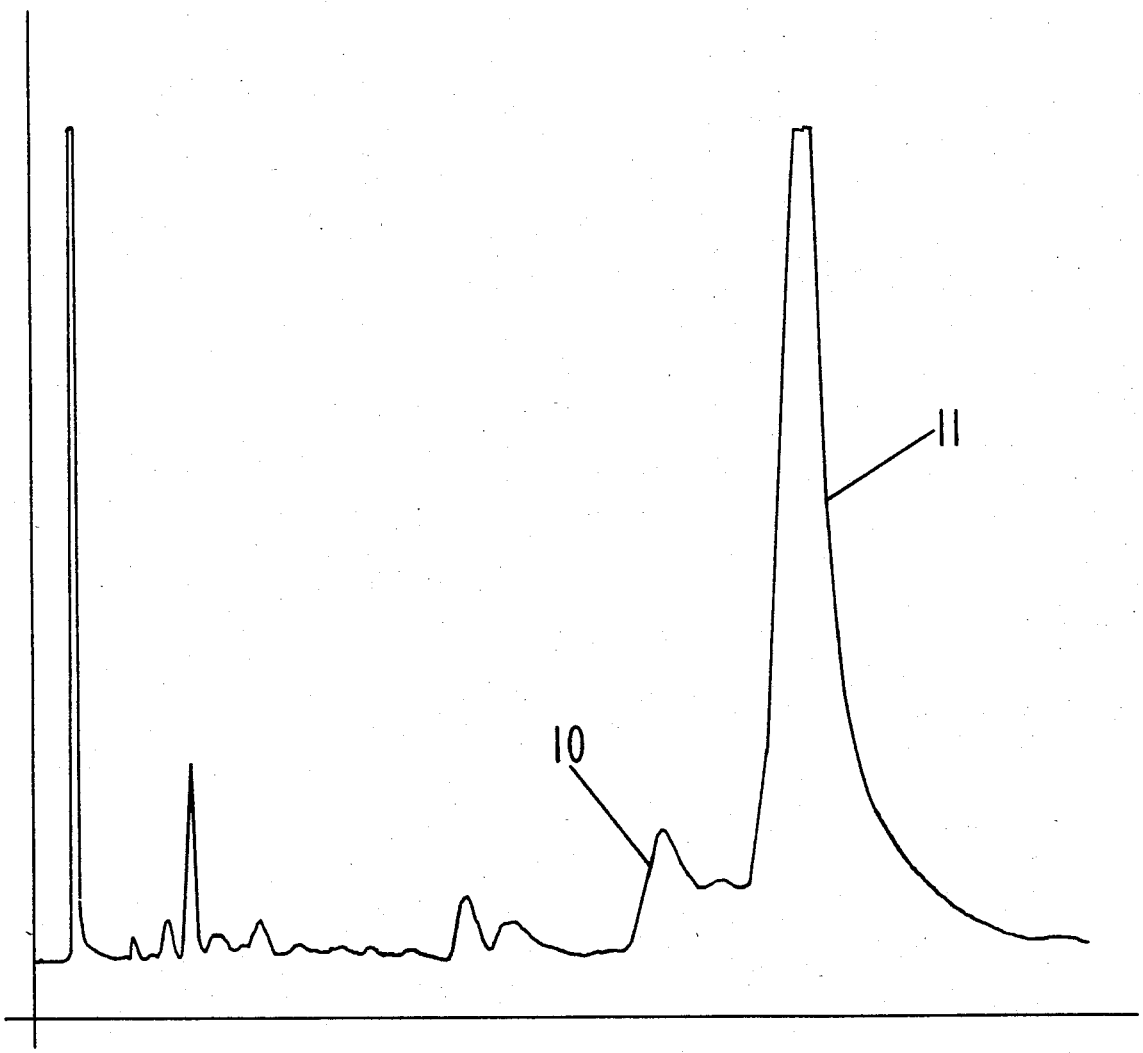
FIG. 1 is the GLC profile for Fraction 8 of the distillation product of the reaction product of Example I containing the compounds having the structures.

FIG. 1 is the GLC profile for Fraction 8 of the distillation product of the reaction product of Example I. The peak indicated by reference numeral "10" in FIG. 1 is the peak for a mixture of compounds defined according to the structures:

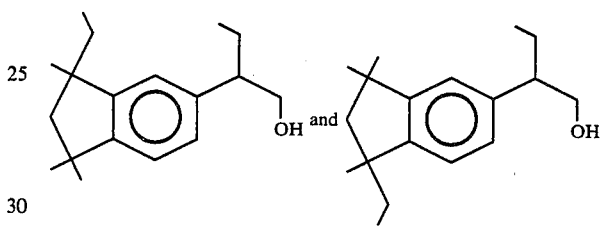

The peak indicated by reference numeral "12" is the peak for the compound having the structure:

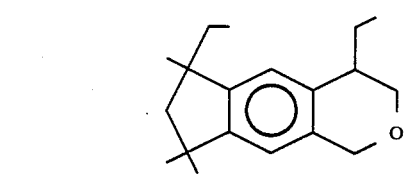

FIG. 4 is the GLC profile for the crude reaction product of Example II. The peak indicated by reference numeral "40" is for the compound defined according to the structure:

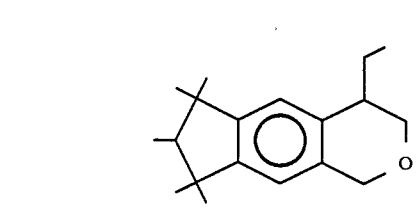

The peak indicated by reference numeral "41" is for the compound having the structure:

THE INVENTION

It has now been discovered that novel solid and liquid foodstuff, chewing gum, medicinal product and flavoring compositions therefor having pear, peach and apricot flavors with sweet, musky aroma and flavor characteristics; and novel perfume compositions and perfumed articles having sweet, musky aromas may be provided by the novel isochroman derivatives defined according to the generic structure:

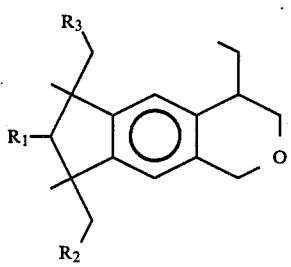

wherein $R_1$, $R_2$ and $R_3$ represent methyl or hydrogen with the proviso that when one of $R_1$, $R_2$ and $R_3$ is methyl; the other of $R_1$, $R_2$ and $R_3$ represents hydrogen.

More specifically, the tricyclic isochroman compounds of our invention may be represented by the structures:

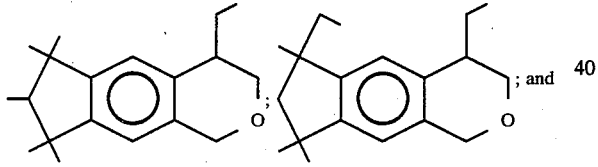

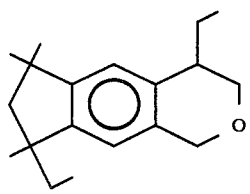

The compounds of our invention may be prepared by first carrying out a Diels Alder reaction of isoamylene with alpha methyl styrene to produce ethyl trimethyl indane and pentamethyl indane in admixture according to the reaction:

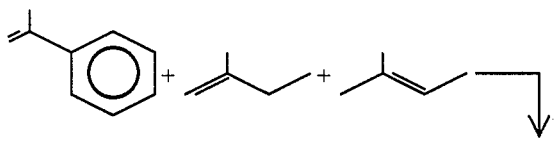

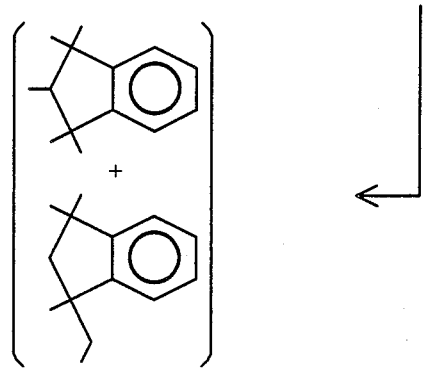

wherein large quantities of the compound:

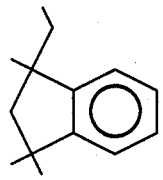

are produced. This reaction is carried out in the presence of a sulfuric acid catalyst in aqueous media at 5° C. or in the presence of a solid hetergeneous catalyst at high temperatures in a pressure apparatus. Depending upon the reactions conditions, the theoretical yield of the mixture of two products having the structures:

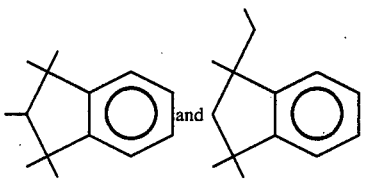

can vary from 30% up to 80%. The ratio of the two products produced varies according to the conditions used. The catalysts used can be either 70% sulfuric acid (at low temperatures, e.g., 35° C.) or can be acid clays, such as Filtrol ®2, "SPA-2" ® (a Universal Oil Products catalyst which is phosphoric acid adsorbed onto clay) or an acid ion exchange resins, such as Amberlyst ®15 (produced by the Rohm & Haas Company, Philadelphia, Pa.) or Dowex ®50 (produced by the Dow Chemical Company, of Midland, Mich.).

The mole ratio of the isoamylene to alpha methyl styrene should be between 1:1 and 2:1. The reaction can be carried out in the presence of or in the absence of a solvent and it is preferable that the reaction be carried out in the absence of solvent when using the heterogeneous catalyst as stated above and, supra. When solvent is desired to be used, such solvents as aliphatic hydrocarbons and aliphatic chlorocarbons may be used, for example, methylene dichloride, n-hexane, n-heptane, n-octane, n-nonane, 2,4,4-trimethyl pentane and the like. The ratio of catalyst to reactants can vary between 0.1% and 8% of the total weight of alpha methyl styrene and isoamylene used. The reaction temperature can vary from 75° C. up to 250° C.; preferably between 100° and 200° C. The pressure for carrying out this reaction depends on the temperature of reaction and the catalyst and can vary from 50 psig to 300 psig when using a heterogeneous catalyst and is atmospheric pressure when using the aqueous 70% sulfuric acid catalyst. The reaction can be carried out batch-wise, continuous or semi-batch. In carrying out the batch process, solvent is first charged to the reactor (such as Primol ®, a hydrocarbon mineral oil (produced by the Exxon Corporation of Linden, N.J.) and the catalyst is then charged into a pressure vessel. Using a pressure pump, a mixture of amylene and alpha methyl styrene is pumped into the pressure vessel preheated to a specified temperature over a period of from about 2 up to about 10 hours. At the end of the feeding of the mixture, the vessel is stored in a quiescent state for a period of up to 5 hours. The pressure vessel is then cooled and the catalysts are removed by filtration and the product is purified by distillation.

In a continuous process, a pressure-rated tube is charged with catalyst and heated to the desired temperature. The mixture of amylene and alpha methyl styrene (and solvent, if desirable) is pumped through the tube and may be recycled several times. The resulting reaction mass is then distilled to yield the desired product.

The following table (Table I) indicates the results of carrying out batch reactions over a five-hour reaction time and five-hour age time. GLC peak I represents the compound having the structure:

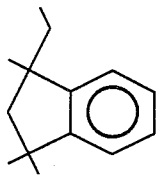

GLC peak II represents the compound having the structure:

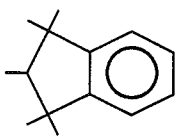

| Weight of Alpha Methyl Styrene | Weight of Amylene | Catalyst and gms. | Temp. ° | GLC Results % Peak 1 | GLC Results % Peak II |
|---|---|---|---|---|---|
| 590 | 400 | Filtrol 105 25 gm. | 175 | 29 | 24 |
| 590 | 400 | SPA-2 25 gm. | 175 | 28 | 25 |
| 590 | 400 | SPA-2 25 gm. | 150 | 25 | 28 |
| 590 | 400 | SPA-2 25 gm. | 125 | 12.5 | 30.5 |
| 590 | 400 | Si—Al 25 gm. | 150 | 25 | 41 |
| 590 | 400 | Si—Al 25 gm. | 125 | 6 | 15 |
| 590 | 400 | Filtrol 13 25 gm. | 100 | 24 | 33 |
| 590 | 400 | Filtrol 13 50 gm. | 100 | 26 | 28 |

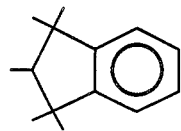

| Weight of Alpha Methyl Styrene | Weight of Amylene | Catalyst and gms. | Temp. ° | GLC Results % Peak 1 | GLC Results % Peak II |
|---|---|---|---|---|---|
| 590 | 400 | Filtrol 13 50 gm. | 125 | 28 | 26 |
| 590 | 400 | Filtrol 13 25 gm. | 125 | 28 | 29 |
| 590 | 400 | Filtrol 13 12.5 gm. | 125 | 24 | 29 |

The resulting mixture of hydrocarbons having the structures:

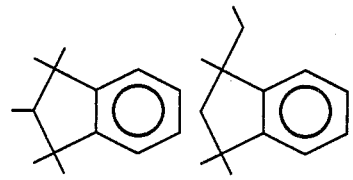

and small amounts of the compound having the structure:

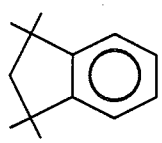

(less than 1%) is then reacted with 1,2-butane epoxide in the presence of a catalyst to produce the indane alkanols according to the reaction:

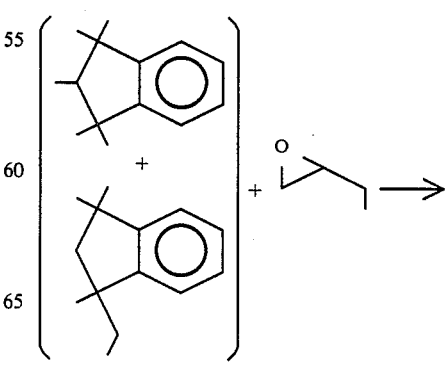

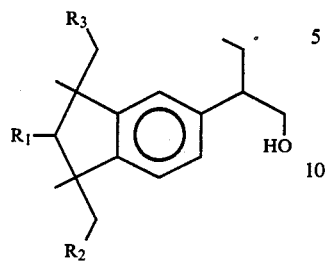

wherein one of $R_1$, $R_2$ and $R_3$ is methyl and the other two of $R_1$, $R_2$ and $R_3$ represent hydrogen using the conditions of Example XV of U.S. Pat. No. 3,360,530 the conditions of U.S. Pat. No. 3,532,719.

The resulting indane alkanol mixture is then separated and is used as an intermediate in order to make tricyclic isochroman derivatives by first reacting the mixture of indane alkanols with a mixture of a $C_1$–$C_3$ lower alkanol and formaldehyde or a formaldehyde precursor such as a mixture of paraformaldehyde and isopropanol according to the reaction:

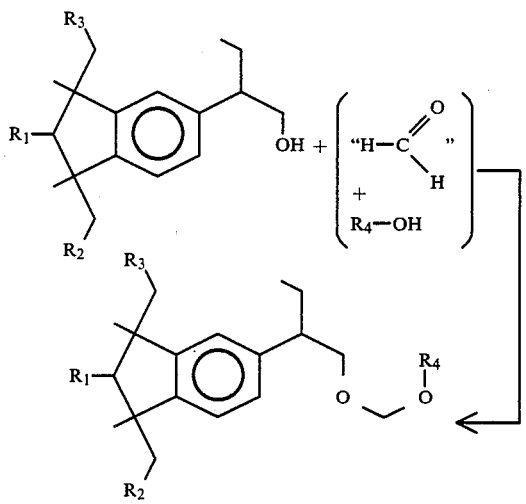

wherein $R_4$ represents $C_1$–$C_6$ lower alkyl and $R_1$, $R_2$ and $R_3$ are defined, supra.

More specifically, such reaction can be illustrated thusly:

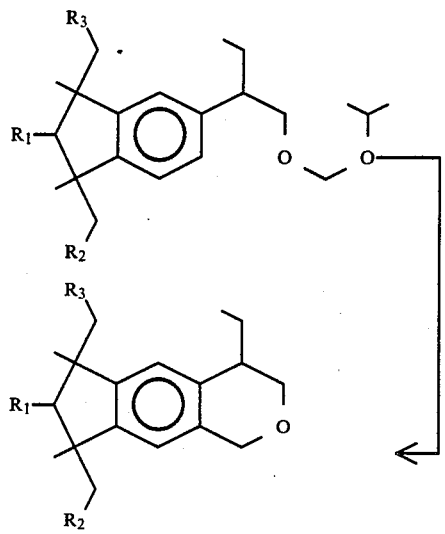

after first forming the diacetal according to the reaction:

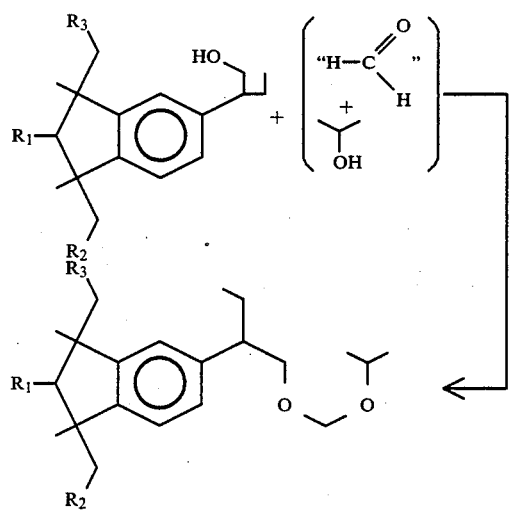

The conditions of the reaction are set forth and exemplified in U.S. Pat. No. 3,978,090 issued on Aug. 31, 1976, the specification for which is incorporated by reference herein. Thus, the cyclization is carried out:
 (a) in the presence of a protonic acid selected from the group consisting of paratoluene sulfonic acid and phosphoric acid; and
 (b) in the presence of an azeotroping agent selected from the group consisting of n-hexane, cyclohexane, methyl cyclohexane, benzene and toluene.

The reaction is carried out by simultaneously (i) heating the resulting mixture for a period of time whereby a substantial amount of the isochroman having the above structure is formed while (ii) azeotropically removing water of reaction with the azeotroping agent.

The acid concentration in the reaction may be in the range of from 1% up to 100% weight/weight based on the total weight of other reagents charged. The preferred range depends upon the acid used. Two preferred acids which may be used are phosphoric acid and p-toluene sulfonic acid. When 85% phosphoric acid is used, the preferred concentration is 1% to 50% weight of acid based on the total weight of other reagents used.

Where the acetal is fored in situ, it is formed by reaction of an aldehyde and lower alkanol such as isopropanol. The concentration of the aldehyde may be in the range of 0.1 mole up to 100 moles or more per mole of indane alkanol. The preferred rannge is 1-5 moles of formaldehyde per mole of indane alkanol. The lower alknaol used to react with the formaldehyde to form the acetal may be used in the concentration of from 0.1-100 moles per mole of indane alkanol. If the formaldehyde is taken in less than 0.5 moles per mole of indane alkanol, it is probably not necessary to use more than 0.1 moles of lower alkanol per mole of indane alkanol.

When the formaldehyde or formaldehyde precursor is taken in an amount greater than 0.5 mole per mole of indane alkanol, the lower alkanol, e.g., isopropyl alcohol should be taken in an amount at least equal to twice the difference between the number of moles of formaldehyde and half the number of moles of indane alkanol whereby it is insured that all of the formaldehyde or formaldehyde precursor is converted into an acetal to prevent self condensation of the formaldehyde under acidic reaction conditions. It is preferred to use an excess of lower alkanol, e.g., isopropanol over that required for complete conversion of the aldehyde to the acetal. If desired, the lower alkanol, e.g., isopropanol can also be used as a solvent for the reaction mass.

The reaction temperature may be in the range of 0° C. up to 200° C., with the range of 80°-95° C. being particularly preferred.

The reaction pressure for this cyclization to form the isochroman may be equal to, above or below atmospheric pressure so long as the necessary reaction temperature is obtained to give a reasonable rate of conversion to the isochroman. By suitable choice of reagents it is possible to carry out the reaction smoothly at atmospheric pressure, thereby avoiding the necessity of using more expensive pressure or vacuum equipment.

After the reaction of our invention to form the isochroman, the reaction mass is neutralized with aqueous base such as aqueous sodium hydroxide or potassium hydroxide solution and the washed mixture is then treated by conventional techniques such as distillation, extraction, preparative chromatography, and the like, to obtain highly purified isochroman. Fractional distillation is a preferred method of recovering the isochroman.

When the ethyl substituted tricyclic isochroman mixture of our invention are used as food flavor adjuvants, the nature of the co-ingredients included with said ethyl substituted tricyclic isochroman mixture in formulating the product composition will serve to alter the organoleptic characteristics of the ultimate foodstuff treated therewith.

As used herein in regard to flavors, the terms "alter" and "modify" in their various forms means "supplying or imparting flavor character or note to otherwise bland, relatively tasteless substances or augmenting the existing flavor characteristic where a natural flavor or synthetic flavor or mixture of natural and synthetic flavors is deficient in some regard, or supplementing the existing flavor impression to modify its quality, character or taste".

As used herein, the term "enhance" is intended to mean the intensification (without effecting a change in kind of quality or aroma or taste) of one or more taste and/or aroma nuances present in the organoleptic impression of a consumable material, e.g., foodstuff, tobacco, chewing gum, medicinal product, perfume composition or perfumed article.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "chewing gum" is intended to mean a composition which comprises a substantially water-insoluble, chewable plastic gum base such as chicle, or substitutes therefor, including jelutung, guttakay rubber and/or certain comestible natural or synthetic resins or waxes. Incorporated within the gum base, in admixture therewith may be plasticizers or softening agents, e.g., glycerine; and a flavoring composition which incorporates the ethyl substituted tricyclic isochroman mixture of our invention, and, in addition, sweetening agents which may be sugars, including sucrose or dextrose and/or artificial sweeteners including dipeptides, cyclamates and saccharin. Other optional ingredients may also be present.

The term "medicinal product" includes both solids and liquids which are ingestible, non-toxic materials having medicinal value such as cough syrups, cough drops, toothpaste, aspirin and chewable medicinal tablets as further exemplified herein.

Substances suitable for use herein as co-ingredients or flavoring adjuvants are well known in the art for such use being extensively described in the relevant literature. Such material is required to be "ingestibly" acceptable and thus non-toxic or otherwise non-deleterious. Particularly critical is the additional requirement that such material be organoleptically compatible with the ethyl substituted tricyclic isochroman encompassed within the scope of our invention. Also critical is the additional requirement that such material be nonreactive (within the range of storage conditions and room temperature use conditions) with ethyl substituted tricyclic isochromans.

Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene, (2,6-di-tertiary-butyl-4-methyl phenol), propyl gallate and the like and sequestrants, e.g., citric acid.

Thickener compounds include carriers, binders, protective colloids, suspending agents, emulsifiers, and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates, starches, pectins, and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, plamitic acid, myristic acid and the like, mono- and diglycerides of fatty acids, lecithin, defoaming and flavor-dispersing agents, such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anticaking agents, e.g., aluminum calcium sulfate and tribasic calcium phosphate; enzymes, yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, cis and trans 2-methyl-2-pentenoic acid, and cis and trans 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethyl-acrolein, n-hexanal, 2-hexenal, cis-3-hexenal, 2-heptenal, 4-(p-hydroxyphenyl)-2-butanone, alpha-ionone, beta-ionone, methyl-3-butanone, 2-pentanone, 2-pentenal and propanal; alcohols such as 1-butanol, benzyl alcohol, 1-borneol, trans-3-buten-1-ol, ethanol, geraniol, 1-hexanol, 2-heptenol-1, trans-3-hexenol-1, cis-3-hexen-1-ol, 3-methyl-3-buten-1-ol, 1-penten-2-ol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate, ethyl caproate, ethyl cinnamate, ethyl crotonate, ethyl formate, ethyl isobutyrate, ethyl isovalerate, ethyl alphamethylbutyrate, ethyl propionate, ethyl salicylate, trans-2-hexenyl acetate, hexyl acetate, 2-hexenyl butyrate, n-hexyl butyrate, isoamyl acetate, isopropyl butyrate, methyl acetate, methyl-n-butyrate, methyl caproate, methyl isobutyrate, alpha-methyl-n-butyrate, n-propyl acetate, n-amyl acetate, n-amyl-n-butyrate, benzyl salicylate, dimethyl anthranilate, ethyl methylphenylglycidate, ethyl succinate, isobutyl cinnamate, and terpenyl acetate; lactones, such as delta-decalactone, delta-undecalactone, delta-nonyl-lactone, gamma-undecalactone, gamma-dodecalactone and gamma nonyl-lactone as well as "peach" lactones; essential oils, such as jasmine absolute, rose absolute, orris absolute, lemon essential oil, Bulgarian rose, yara yara, natural raspberry oil and vanilla; sulfides, e.g., methyl sulfide and other materials such as maltol, acetoin, acetals (e.g., 1,1-diethoxyethane, 1,1-dimethoxyethane and dimethoxymethane) and 2- and 3-cyclotetradecene-1-ones having one of the structures:

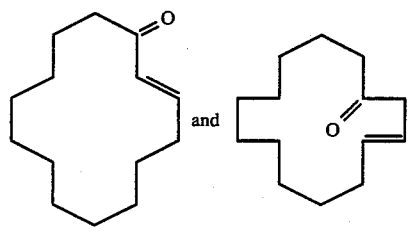

described in application for U.S. patent Ser. No. 973,093 filed on Dec. 26, 1978, now U.S. Pat. No. 4,183,965.

The specific flavoring adjuvant selected for use may be either solid or liquid depending upon the desired physical form of the ultimate product, i.e., foodstuff whether simulated or natural, and should, in any event, be capable of providing an environment in which the ethyl substituted tricyclic isochroman mixture of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted.

In contradistinction, in the preparation of solid products, e.g., simulated foodstuffs, ingredients capable of providing normally solid compositions should be selected such as various cellulose derivatives.

As will be appreciated by those skilled in the art, the amount of ethyl substituted tricyclic isochroman mixture of our invention employed in a particular instance can vary over a relatively wide range whereby specific desired organoleptic effects (having particular reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify, or enhance the organoleptic characteristics of the parent composition, whether foodstuff per se or flavoring composition.

The use of insufficient quantities of ethyl substituted tricyclic isochroman mixture of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it has been found that quantities of ethyl substituted tricyclic isochroman mixture of our invention ranging from a small but effective amount, e.g., 0.0001 parts per million up to about 50 parts per million by weight based on total composition are suitable. Concentrations in excess of the maximum quantity stated are not normally recommended, since they fail to provide commensurate enhancement or augmentation of organoleptic properties. In those instances wherein the ethyl substituted tricyclic isochromans are added to the foodstuff as an integral component of a flavoring composition, it is, of course, essential that the total quantity of flavoring composition employed be sufficient to yield an effective concentration (of ethyl substituted tricyclic isochromans) in the foodstuff product.

Food flavoring compositions prepared in accordance with the present invention contain the ethyl substituted tricyclic isochromans in concentrations ranging from about 0.01% up to about 15% by weight based on the total weight of the said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the ethyl substutited tricyclic isochromans with, for example, gum arabic, gum tragacanth, carrageenan and the like, and thereafter spray drying the resultant mixture whereby to obtain the particulate solid product. Preprepared flavor mixes in powder form, e.g., a fruit-flavored powder mix are obtained by mixing the dried solid components, e.g., starch, sugar and the like and ethyl substituted tricyclic isochromans in a dry blender until the requisite degree of uniformity is acheived.

It is presently preferred to combine with ethyl substituted tricyclic isochromans, the following adjuvants:
p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
β-Damascone;
β-Damascenone;
Ethyl butyrate;
Acetic acid;
n-Hexyl acetate;
n-Hexyl isobutyrate;
Trans-2-hexenal;
Linalyl isobutyrate;
n-Hexyl-2-methyl-n-butyrate;
Gamma-undecalactone;
Gamma-nonalactone;
Gamma-decalactone;
Delta undecalactone;
Delta dodecalactone;
Delta nonyl lactone;
"Peach" lactone;
Naphthyl ethyl ether;
Diacetyl;
Apple Fusel Oil;
Sauge Sclaree;
Coriander Oil;
Ethyl acetate;
Anethole;
Isoamyl-n-butyrate;
Ethyl-2-methyl-cis-3-pentenoate;
Cis-3-hexenol-1;
2-Methyl-cis-3-pentenoic acid;
2-Methyl-2-pentenoic acid;
Elemecine (4-allyl-1,2,6-trimethoxy benzene);
Isoelemecine (4-propenyl-1,2,6-trimethoxy benzenne);
2-(4-hydroxy-4-methylpentyl)norbornadiene prepared according to U.S. Pat. No. 3,886,289; and
2- and 3-Cyclotetradecen-1-ones having the structures:

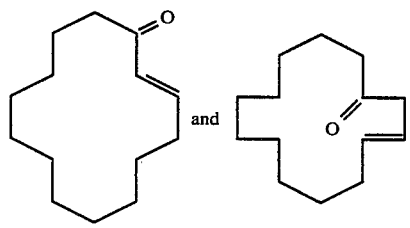

described according to application for U.S. patent, Ser. No. 973,093 filed on Dec. 26, 1978, now U.S. Pat. No. 4,183,965.

The ethyl substituted tricyclic isochromans and one or more auxiliary perfume ingredients including, for example, alcohols other than the ethyl substituted tricyclic isochromans of our invention, aldehydes, nitriles, esters, cyclic esters, ketones, ethers other than the tricyclic isochromans of our invention, natural essential oils and synthetic essential oils, may be admixed so that the combined odors of the individual components produce a pleasant and desired fragrance, particularly and preferably, in musk and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to its particular olfactory characteristics, but the over-all effect of the perfume composition will be the sum of the effects of each of the ingredients. Thus, the ethyl substituted tricyclic isochromans can be used to alter the aroma characteristics of a perfume composition, for example, by utilizing or moderating the olfactory reaction contributed by at least one other ingredient in the composition.

The amount of the ethyl substituted tricyclic isochromans of our invention which will be effective in perfume compositions depends on many factors including the other ingredients, their amounts and the effects which are desired. It has been found that perfume compositions containing as little as 0.01% of ethyl substituted tricyclic isochromans and even less (e.g., 0.005%) can be used to impart sweet, musky aromas with earthy and minty and sweet nuances to soaps, anionic, cationic and nonionic detergents, fabric softener articles and compositions of matter, cosmetics or other products. The amount employed can range up to 10% of the fragrance components and can range up to 0.5% of the weight of the perfumed article and will depend upon considerations of cost, nature of the end product, the effect desired on the finished product and the particular fragrance sought.

The ethyl substituted tricyclic isochromans are useful, taken alone or in perfume compositions as olfactory components in anionic, cationic and nonionic detergents, soaps, fabric softener compositions, fabric softener articles for use in clothes dryers (e.g., "BOUNCE" ®, a registered trademark of the Procter & Gamble Company of Cincinnati, Ohio), space odorants and deodorants, perfumes, colognes, toilet water, bath preparations, such as bath oils, and bath solids; hair preparations, such as lacquers, brilliantines, creams, deodorants, hand lotions and sun screens; powders, such as talcs, dusting powders, face powders and the like. When used as an olfactory component in perfume compositions or perfumed articles, such as anionic, cationic and nonionic detergents and in fabric softener compositions and fabric softener articles (e.g., for use in clothing dryers) as little as 0.05% of the ethyl substituted tricyclic isochromans of our invention will suffice to impart an intense sweet musk fragrance with earthy and minty nuances. Generally, no more than 5% of the ethyl substituted tricyclic isochromans based on the ultimate end product is required in the perfume composition or in the perfumed article.

In addition, the perfume composition or fragrance composition of our invention can contain a vehicle or carrier for the ethyl substituted tricyclic isochromans. The vehicle can be a liquid such as a non-toxic alcohol, a non-toxic glycol, or the like. The carrier can also be an absorbent solid, such as a gum (e.g., gum arabic) or components for encapsulating the composition (such as gelatin) as by means of coacervation.

It will thus be apparent that the ethyl substituted tricyclic isochromans of our invention can be utilized to alter the sensory properties, particularly organoleptic properties, such as flavors and/or fragrances of a wide variety of consumable materials.

The following examples are illustrative and the invention is to be considered restricted thereto only as indicated in the appended claims. All parts and percentages given herein are by weight unless otherwise specified.

EXAMPLE "A-1"

PREPARATION OF PENTAMETHYL INDANE AND TRIMETHYL ETHYL INDANE MIXTURE

Reaction:

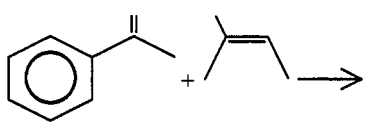

-continued

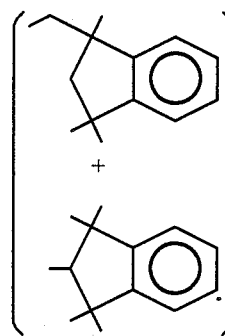

Into a 2-liter stirring autoclave (Parr) is charged 150 grams of Primol ® and 25 grams of Filtrol 13 ®. The autoclave is then flushed with nitrogen and heated to 125° C. 590 Grams of alpha methyl styrene and 400 grams of amylene in admixture is pumped into the autoclave over a period of 5 hours. The autoclave contents is then stirred for an additional 5 hours.

Five batches are combined and the catalyst is removed by filtration. The filtrate is distilled through a Goodloe packed column (8"×1-½") at a reflux ratio of 4:1:

| Fraction No. | Vapor Temp. (°C.) | Liquid Temp. (°C.) | Vacuum mm/Hg. Pressure | Weight of Fraction (grams) |
|---|---|---|---|---|
| 1-6 | 64 | 125 | 50-4.8 | 273 |
| 7-11 | 63-70 | 110-116 | 3.8 | 374 |
| 12-25 | 70-74 | 116-139 | 3.8-4.6 | 1817 |
| 26 | 78 | 144 | 4.5 | 172 |
| 27-32 | 81-90 | 144-156 | 1.8 | 471 |
| 33-38 | 103-116 | 167-235 | 2.5 | 1091 |
| | | | Residue: | 215 |

GLC analysis shows the following:
| | |
|---|---|
| Fractions 1-6 | Mainly recovered C5 hydrocarbons |
| Fractions 7-11 | 11% Tetramethyl indane, 44% Ethyl trimethyl indane and 31% Pentamethyl indane. |
| Fractions 12-25 | 46% Ethyl trimethyl indane and 51% Pentamethyl indane. |
| Fractions 26 | 15% Ethyl trimethyl indane and 67% Pentamethyl indane. |
| Fractions 27-32 and 33-38 | Mainly trimers of amylene and dimers of alpha methyl styrene. |

Fractions 7-26 represent a yield of approximately 50% of theory based on alpha methyl styrene.

FIG. "A" is the GLC profile of the reaction product prior to distillation (conditions: 5% carbowax, 10'×0.25", column programmed at 125° C. isothermal). The peak indicated by reference numeral "1" is the peak for the compound having the structure:

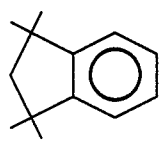

The peak indicated by reference numeral "2" is the peak for the compound having the structure:

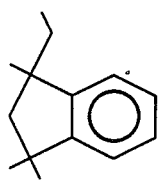

The peak indicated by reference numeral "3" is the peak for the compound having the structure:

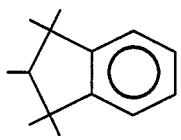

The peaks indicated by reference numeral "4" is the peaks for the dimers of isoamylene.

The peak indicated by the reference numeral "5" is the peak for alpha methyl styrene dimers.

The foregoing example is substantially identical to that which is set forth as Example I, at column 15 and 16 of U.S. Pat. No. 4,265,818 (the specification for which is incorporated by reference herein). When the Filtrol ® 13 catalyst is replaced with sulfuric acid and the temperature of reaction is 35° C. and the reaction is carried out for 15 hours at atmospheric pressure substantially results are obtained.

EXAMPLE I

PREPARATION OF PENTAMETHYL INDANE-3-BUTANOL-1

Reaction:

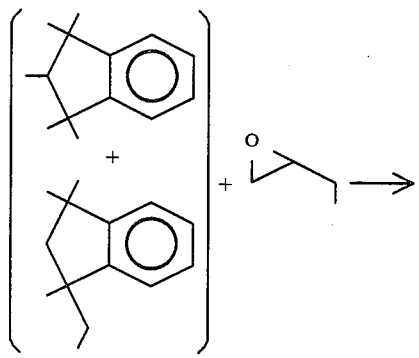

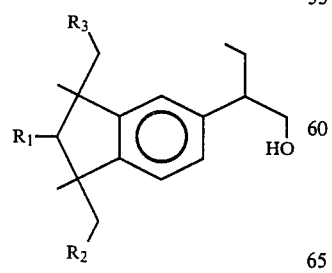

A mixture of 1970 grams of the hydrocarbon mixture containing the compounds having the structures:

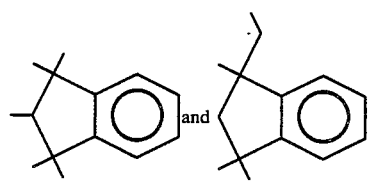

with 492 grams of Isopar ® E (a mixture of predominant C-8 alaphatic hydrocarbons available from Exxon) is made up and 1600 grams of this mixture is placed in a 5-liter reaction flask equipped with stirrer, thermometer, reflux condensor, addition funnel and nitrogen inlet tube. The reaction mass is cooled to −5° C. and 534 grams of aluminum chloride is added to the reaction mixture. Into a dropping funnel is placed 862 grams of the mixture of hydrocarbons having the structures:

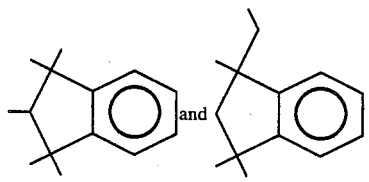

prepared according to Example A-1 and 288 grams of 1,2-butane epoxide. Over a three hour perod, while maintaining the reaction mass in minus 5°-10° C., the 1,2-butane epoxide/indane hydrocarbon-Isopar ® E mixture is added to the reaction mass with stirring.

At the ends of the reaction, the reaction mass is poured into 3-liters of crushed ice and 2-liters of water and stirred for 15 minutes. The reaction mass is then washed as follows:

(a) 1-liter of water;
(b) 1-liter of water and 10 ml 50% sodium hydroxide

The reaction mass is then distilled on a 4" splash column yielding the following fractions:

| Fraction No. | Vapor Temp. (°C.) | Liquid Temp. (°C.) | Vacuum mm/Hg. Pressure |
|---|---|---|---|
| 1 | 67/70 | 95/96 | 3.0/3.0 |
| 2 | 79 | 105 | 3.0 |
| 3 | 87 | 109 | 3.0 |
| 4 | 95 | 115 | 3.0 |
| 5 | 84 | 125 | 3.0 |
| 6 | 98 | 146 | 3.0 |
| 7 | 125 | 165 | 1.0 |
| 8 | 145 | 175 | 1.0 |
| 9 | 137 | 210 | 1.0 |
| 10 | 121 | 210 | 1.0 |

Fractions 1–7 represent recovered solvents, unreacted indane having the structures:

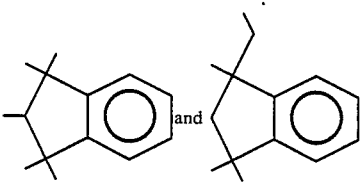

and Isopar ® E.

Fractions 8, 9 and 10 represent the product defined according to the structures:

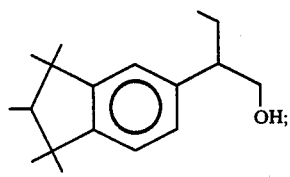

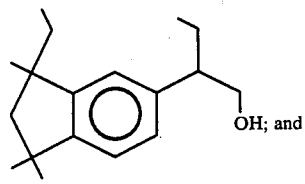

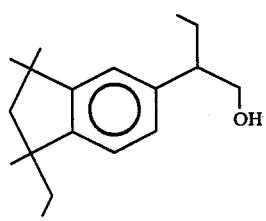

FIG. 1 is the GLC profile for Fraction 8 of the foregoing distillation (conditions: S.E. 30, column programmed at 220° C. isothermal). The peak indicated by reference numeral "10" is the peak for the mixture of compounds defined according to the structures:

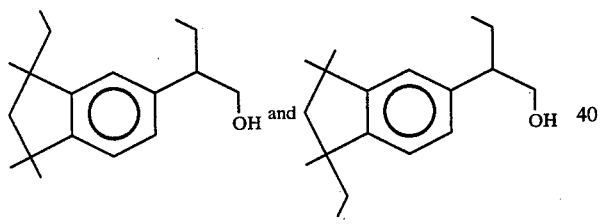

The peak indicated by reference numeral "11" is the peak for the compound having the structure:

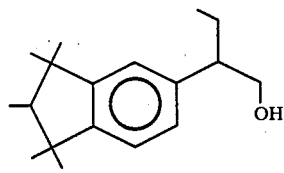

FIG. 2 is the NMR spectrum for the compound having the structure:

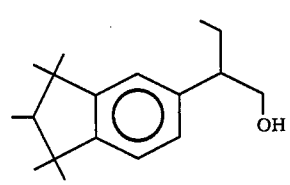

(conditions: $CFCl_3$ solvent; field strength 100 MH$_z$).

FIG. 3 is the infra-red spectrum for the compound having the structure:

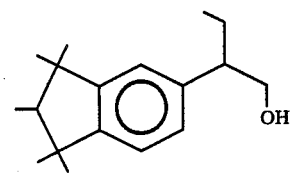

EXAMPLE II

PREPARATION OF
6-OXA-1,1,2,3,3-PENTAMETHYL-8-ETHYL-2,3,5,6,7,8-HEXAHYDRO-1H-BENZ(f)-INDENE;
6-OXA-1,1,3-TRIMETHYL-2,8-DIETHYL-2,3,5,6,7,8-HEXAHYDRO-1H-BENZ(f)-INDENE;
AND
6-OXA-1,3,3-TRIMETHYL-2,8-DIETHYL-2,3,5,6,7,8-HEXAHYDRO-1H-BENZ(f)-INDENE
ADMIXTURE AND SEPARATE COMPOUNDS

Reaction:

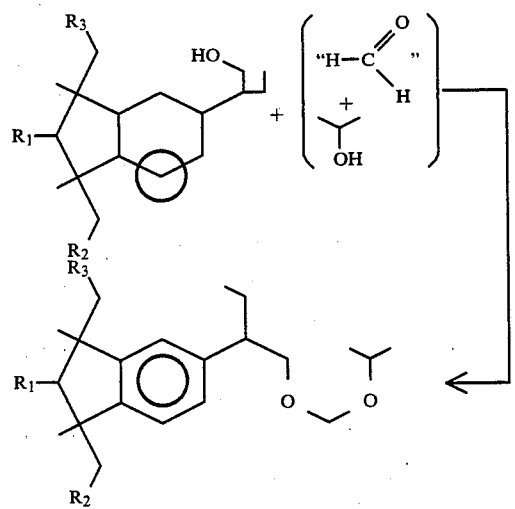

and

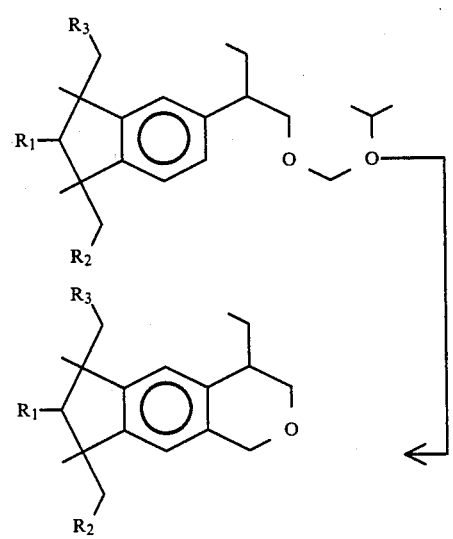

(wherein referring to mixtures of compounds as reactants and products, in each of the molecules of the mixtures one of $R_1$, $R_2$ and $R_3$ represents methyl; and each of the other two of $R_1$, $R_2$ and $R_3$ represent hydrogen).

Into a 3-liter reaction flask equipped with stirrer, thermometer, reflux condensor and heating mantle is placed 550 grams of bulked Fractions 8, 9 and 10 of the distillation product of the reaction product of Example I containing the compounds having the structures:

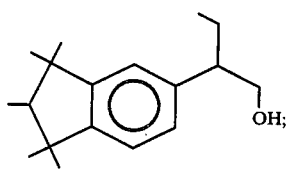

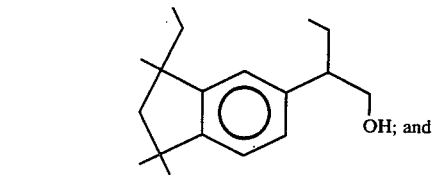

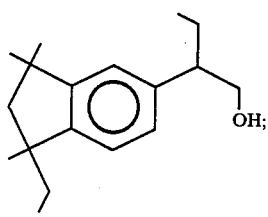

52 grams paratoluene sulfonic acid; 195 grams isopropyl alcohol; 130 grams toluene and 99 grams of paraformaldehyde.

The resulting mixture is heated to reflux and maintained at reflux for a period of 2 hours (90° C.). At the end of the 2 hour period, solvent is stripped up to 135° C. The reaction product is then cooled to 80° C. and 200 ml toluene and 400 ml 10% aqueous sodium hydroxide is added to the reaction mass. The reaction mass is stirred at 80° C. for 15 minutes and then washed with one 1-liter portion of water. The reaction mass is then distilled fractionally on a 6" stone packed column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 95/120 | 164/107 | 2.0/2.0 | 6.7 |
| 2 | 75 | 158 | 2.0 | 10.3 |
| 3 | 82 | 158 | 2.0 | 17.0 |
| 4 | 85 | 159 | 1.8 | 20.7 |
| 5 | 88 | 163 | 4.0 | 24.3 |
| 6 | 88 | 164 | 4.0 | 17.3 |
| 7 | 88 | 164 | 2.5 | 20.6 |
| 8 | 85 | 163 | 4.0 | 31.1 |
| 9 | 85 | 108 | 4.0 | 20.0 |
| 10 | 120 | 175 | 4.0 | 25.1 |
| 11 | 130 | 178 | 3.5 | 30.3 |
| 12 | 127 | 180 | 3.0 | 29.1 |
| 13 | 127 | 178 | 3.0 | 28.0 |
| 14 | 88 | 170 | 5.0 | 36.5 |
| 15 | 85 | 175 | 5.0 | 41.3 |
| 16 | 106 | 200 | 8.0 | 48.6 |
| 17 | 95 | 210 | 8.0 | 13.8 |

Fractions 8-14 are bulked and have a sweet musky, caramel aroma which is intense and long lasting.

The resulting bulking is a mixture of compounds defined according to the structures:

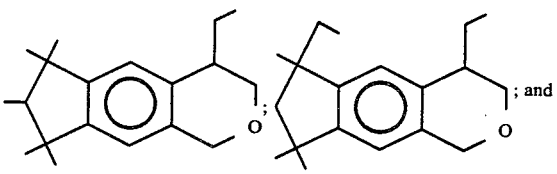

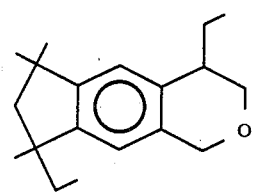

FIG. 4 is the GLC profile for the crude reaction product prior to distillation (conditions: S.E. 30, column programmed at 220° C. isothermal). The peak indicated by reference numeral "40" is the peak for the compound defined according to the structure:

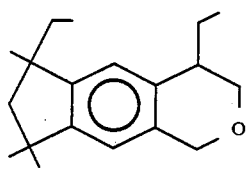

The peak indicated by reference numeral "41" is the peak for the compound having the structure:

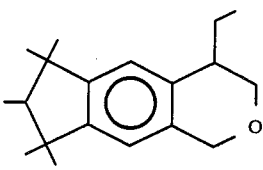

FIG. 5 is the NMR spectrum for Fraction 11 of the foregoing distillation containing the compound having the structure:

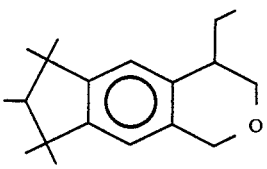

(solvent: $CFCl_3$; field strength 100 $MH_z$).

FIG. 6 is the infra-red spectrum for Fraction 11 of the foregoing distillation containing the compound having the structure:

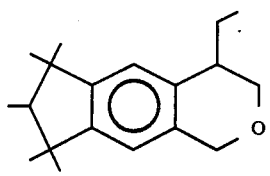

EXAMPLE III

The following basic pear flavor formulation is prepared:

| Ingredients | Parts by Weight |
|---|---|
| Vanillin | 2.0 |
| Hexyl acetate | 8.0 |
| Hexyl isobutyrate | 20.0 |
| Trans-2-hexenal (10% in propylene glycol) | 2.0 |
| n-Hexanal | 0.5 |
| Apple Fusel Oil | 10.0 |
| Linalyl Isobutyrate | 0.5 |
| Hexyl-2-methylbutyrate | 10.0 |
| Sauge Sclaree (10% in propylene glycol) | 0.5 |
| Coriander Oil | 0.5 |
| Food grade ethyl alcohol (aqueous 95%) | 146.0 |
| Propylene glycol | 800.0 |

To a portion of the above basic pear flavor formulation, 0.02% by weight of a mixture containing the following ingredients:

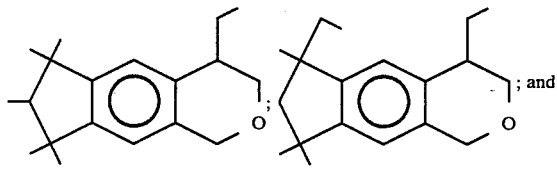

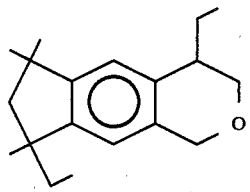

(bulked fractions 8–10 of Example II) is added. To another portion of the basic pear flavor formulation, nothing is added. Both flavor formulations are compared at the rate of 50 ppm in water and evaluated by a bench panel of four experienced tasters. All the tasters of the bench panel state that the flavor containing the mixture of compounds having the structures:

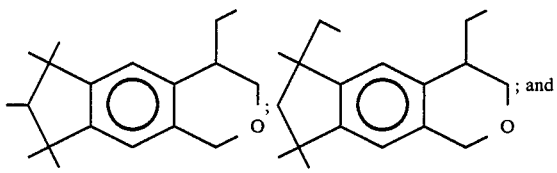

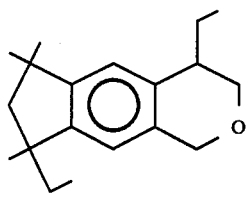

has a more natural riper pear character. This pear character is enhanced and longer lasting as a result of the addition of the mixture of compounds having the structures:

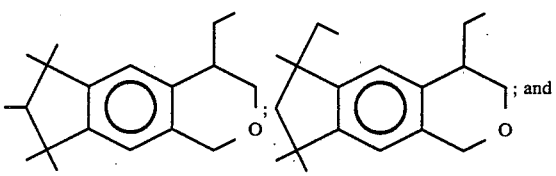

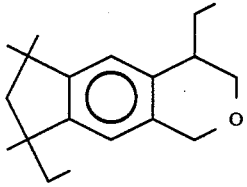

Therefore the flavor formulation containing the compounds having the structures:

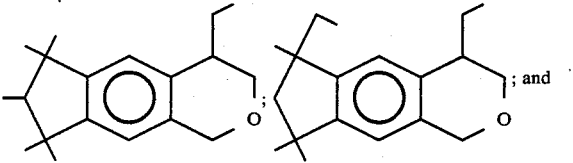

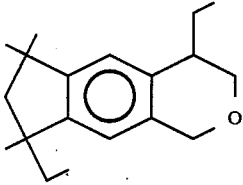

EXAMPLE IV

Granular detergent compositions prepared according to United Kingdom Patent Specification No. 1,501,498 (the specification for which is incorporated by reference herein) having the following formulae is prepared by spray drying the following mixtures:

| | COMPOSITION IN % BY WEIGHT | | | |
|---|---|---|---|---|
| Ingredient | Example VA | Example VB | Example VC | Example VD |
| Sodium salt of ethoxylated fatty alcohol sulfate having an average of about 2.25 moles of ethylene oxide | 14.1 | 14.1 | 14.1 | 14.1 |

-continued

| Ingredient | Example VA | Example VB | Example VC | Example VD |
|---|---|---|---|---|
| per mole of fatty alcohol | | | | |
| Sodium tallow alkyl sulfate | 2.4 | 2.4 | 2.4 | 2.4 |
| Sodium silicate solids ratio: $SiO_2/Na_2O = 2.0$ | 0.0 | 2.0 | 6.0 | 0.0 |
| Sodium silicate solids ratio: $SiO_2/Na_2O = 3.2$ | 1.0 | 0.0 | 0.0 | 6.0 |
| Sodium tripolyphosphate | 24.0 | 24.0 | 24.0 | 24.0 |
| $Na_{12}(AlO_2, SiO_2)$ $27H_2O$ | 18.0 | 18.0 | 18.0 | 18.0 |
| Moisture | 10.0 | 10.1 | 9.9 | 10.2 |
| Sodium sulfate | 25.0 | 25.0 | 20.0 | 20.0 |
| Minor ingredients including sodium toluene sulfonate, trisodium sulfosuccinate, dyes, and brighteners | 4.0 | 2.4 | 3.6 | 2.3 |
| Mixture of tricyclic isochromans (bulked Fraction 8–10) prepared according to Example II | 3.0 | | | |

A laundry solution containing the above detergent compositions is used to launder fabrics. The laundry compositions both prior to and on laundering gives rise to an intense sweet musk aroma.

The composition of this Example IV has a sweet musk aroma in addition to having a faint aesthetically pleasing caramel nuance.

EXAMPLE V

PERFUMED LIQUID DETERGENT

Concentrated liquid detergents with animal-musky aromas are prepared containing 0.10%, 0.15% and 0.20% of tricyclic isochromans prepared according to Example II (bulked Fractions 8–10) having the structures:

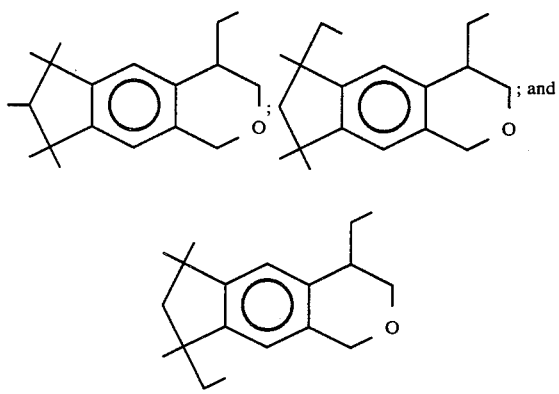

They are prepared by adding and homogeneously admixing the appropriate quantity of tricyclic isochromans in liquid detergent. The liquid detergent is a builder-free liquid detergent consisting of (a) 50% of a non-ionic surfactant having an HLB of 8.0 and a critical micelle concentration of 0.007, weight % at 25° C.; (b) an ionic surfactant which is triethanolamine citrate; and (c) 1 weight % of diethanolamine prepared according to United Kingdom Patent Specification No. 1,491,603.

The detergents all possess sweet musky fragrances, the intensity increasing with greater concentrations of tricyclic isochromans.

EXAMPLE VI

A. Powder Flavor

20 Grams of the flavor composition of Example III which flavor composition contains a mixture of tricyclic isochromans is emulsified in a solution containing 300 grams gum acacia and 700 grams water. The emulsion is spray-dried with a Bowen Lab Model Drier utilizing 250 c.f.m. of air with an inlet temperature of 500° F., and outlet temperature of 200° F. and a wheel speed of 50,000 r.p.m.

B. Paste Blend

The following mixture is then prepared:

| Ingredients | Parts by Weight |
|---|---|
| Liquid Flavor Composition of Example III | 48.4 |
| Cab-O-Sil M-5 (Brand of Silica produced by the Cabot Corporation of 125 High Street, Boston, Mass. 02110); Physical Properties: Surface Area: 200m²/gm Nominal Particle Size: 0.012 microns Density: ⅜ lbs./cu.ft. | 3.2 |

The Cab-O-Sil is dispersed in the liquid flavor composition with vigorous stirring, thereby resulting in a viscous liquid. 48.4 Parts by weight of the powder flavor composition prepared in Part A is then blended into the said viscous liquid, with stirring at 25° C. for a period of 30 minutes, resulting in a thixotropic sustained release flavor paste.

EXAMPLE VII

CHEWING GUM

100 Parts by weight of chicle are mixed with 4 parts by weight of the flavor prepared in accordance with Example VI. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.0 inches in thickness. The strips are cut into lengths of 3 inches each. On chewing, the chewing gum has a pleasant long-lasting pear flavor.

EXAMPLE VIII

TOOTHPASTE FORMULATION

The following separate groups of ingredients are prepared:

| | Group "A" |
|---|---|
| 30.200 | Glycerine |
| 15.325 | Distilled Water |
| .100 | Sodium Benzoate |
| .125 | Saccharin Sodium |
| .400 | Stannous Fluoride |

| | -continued |
|---|---|
| | Group "B" |
| 12.500 | Calcium Carbonate |
| 37.200 | Dicalcium Phosphate (Dihydrate) |
| | Group "C" |
| 2.000 | Sodium n-Lauroyl Sarcosinate (foaming agent) |
| | Group "D" |
| 1.200 | Flavor Material of Example VI |
| 100.00 | (TOTAL) |

PROCEDURE

1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant pear flavor of constant strong intensity throughout said procedure (1–1.5 minutes).

EXAMPLE IX

The flavor material produced according to the process of Example VI(B) is added to a Chewable Vitamin Tablet Formulation at a rate of 5 gm/kg which Chewable Vitamin Tablet Formulation is prepared as follows:

| Ingredients | Parts by Weight |
|---|---|
| Vitamin C (ascorbic acid) as ascorbic acid-solution mixture 1:1 | 70.0 |
| Vitamin B$_1$ (thiamine mononitrate) as Rocoat ® thiamine mononitrate 33% (Hoffman La Roche) | 4.0 |
| Vitamin B$_2$ (riboflavin) as Rocoat ® riboflavin 33⅓% | 5.0 |
| Vitamin B$_6$ hydrochloride) as Rocoat ® pyridoxide hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example VI(B) | 5.0 |
| Sweetener-sodium saccharin | 1.0 |
| Magnesium stearate lubricant | 10.0 |
| Mannitol q.s. to make | 500.0 |

Preliminary tablets are prepared by slugging, with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablet yields a pleasant, long-lasting, consistently strong pear flavor for a period of 12 minutes.

EXAMPLE X

MUSK PERFUME FORMULATION

The following musk perfume formulation is prepared:

| Ingredients | Parts by Weight |
|---|---|
| Musk Ambrette | 200 |
| Musk Ketone | 200 |
| Beta Ionone | 50 |
| Vetiveryl Acetate | 50 |
| Sandalwood Oil | 100 |
| Benzyl Benzoate | 400 |
| Mixture of isochromans (bulked Fractions 8–10) prepared according to Example II | 20 |

The mixture of tricyclic isochromans (bulked Fractions 8–10) of Example II imparts to this musk formulation, a natural "animal-musk" sweet aesthetically pleasing caramellic aroma and causes it to be more "natural-like".

EXAMPLE XI

PREPARATION OF A SOAP COMPOSITION

100 Grams of soap chips are mixed with 1 gram of the perfume composition of Example X until a substantially homogeneous composition is obtained. The perfumed soap composition manifests an excellent animal-musk aroma.

EXAMPLE XII

PREPARATION OF A SOAP COMPOSITION

100 Grams of soap chips are mixed with 1 gram of the tricyclic isochroman mixture prepared according to Example II (bulked Fractions 8–10) until a substantially homogeneous composition is obtained. The perfumed soap composition manifests an excellent musk aroma.

EXAMPLE XIII

PREPARATION OF A COLOGNE AND HANDKERCHIEF PERFUME

The mixture of tricyclic isochromans prepared according to Example II (bulked Fractions 8–10) is incorporated into a cologne at concentrations of 1.5%, 2.0%, 2.5%, 3.0%, 3.5% and 4.0% in 85% aqueous ethanol; and into handkerchief perfumes at concentrations of 15%, 20%, 25% and 30% (in 95% aqueous ethanol). Distinct and definite animal-musk fragrances are produced and imparted to the cologne and to the handkerchief perfume at each of the levels indicated.

EXAMPLE XIV

PREPARATION OF A COSMETIC POWDER COMPOSITION

A cosmetic powder is prepared by mixing in a ball mill, 100 grams of talcum powder with 0.15 grams of the mixture of tricyclic isochromans prepared according to Example II (bulked Fractions 8–10). The resulting powder has an excellent musk aroma with sweet caramellic nuances.

EXAMPLE XV

Utilizing the procedure of Example I of column 15 of U.S. Pat. No. 3,632,396 (the specification for which is incorporated by reference herein), a nonwoven cloth substrate useful as a dryer-added fabric-softening article of manufacture is prepared wherein the substrate, the substrate coating and the outer coating and the perfuming material are as follows:
1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of the mixture of tricyclic isochormans produced according to Example II (bulked Fractions 8-10) having the structures:

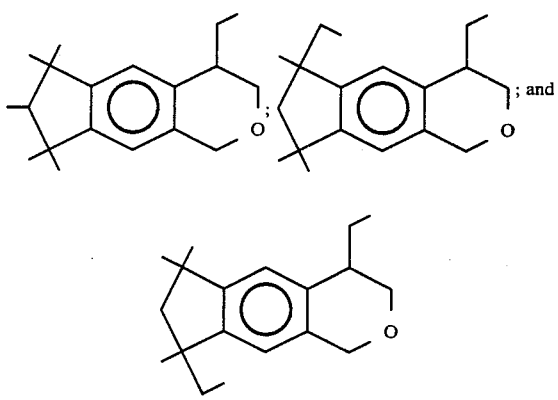

prepared according to Example II.

A fabric-softening composition prepared as set forth above having an aroma characteristic which can be described as sweet and musky with exaltone-like nuances essentially consist of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and an outer coating weight ratio of about 1:1 by weight of the substarate. A sweet, musky, exaltone-like aroma is imparted in a pleasant manner to the head space in the dryer on operation thereof using the said dryer added fabric softening nonwoven fabric.

EXAMPLE XVI

PREPARATION OF A SOAP COMPOSITION

100 Grams of soap chips are prepared according to Example V of U.S. Pat. No. 4,058,490, issued on Nov. 15, 1977 (the specification for which is incorporated by reference herein) as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water, 0.2 lb. titanium hydroxide"

The resulting blend is then mixed with 1 gm of the mixture of compounds (bulked Fractions 8-10) prepared according to Example II containing the compounds having the structures:

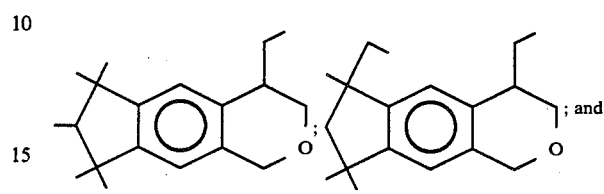

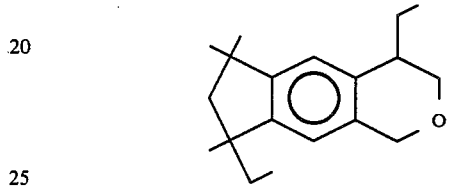

until a substantially homogeneous composition is obtained. The perfumed soap compositions manifests an excellent sweet, musk aroma with excellent aesthetically pleasing caramellic nuances.

What is claimed is:

1. A process for augmenting or enhancing the aroma of a perfume composition, cologne or perfumed article comprising the step of adding to a perfume composition, cologne or perfumed article base an aroma augmenting or enhancing quantity of a product consisting essentially of compounds having the structures:

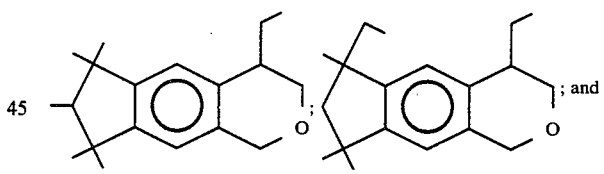

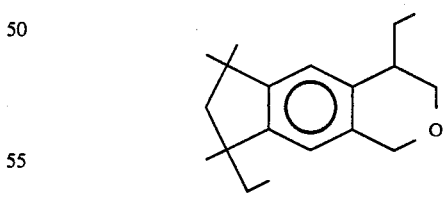

produced according to the process comprising the step of (i) reacting isoamylene with alphamethyl styrene according to the reaction:

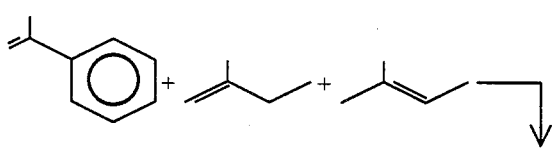

-continued

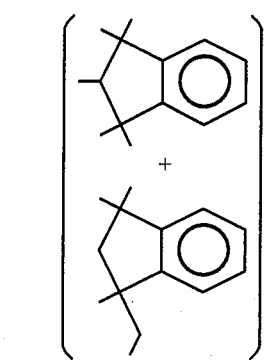

in the presence of a heterogeneous solid catalyst selected from the group consisting of acid clays and acid ion exchange resins, the mole ratio of isoamylene to alpha methyl styrene being 1:1 and 2:1; the ratio of catalyst to reactants being from 0.1% up to 8% of the total weight of alpha methyl styrene and isoamylene; the reaction temperature being between 75° C. and 250° C.; the reaction pressure being between 50 psig and 300 psig; (ii) reacting the resulting product with 1,2-butylene epoxide in the presence of a catalyst to produce a mixture consisting essentially of indane alkanols according to the reaction:

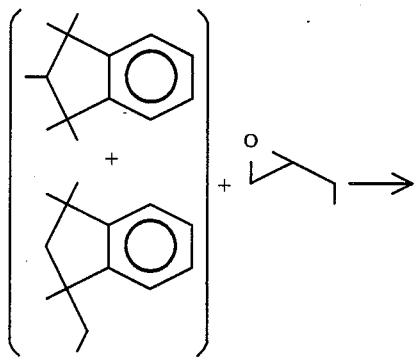

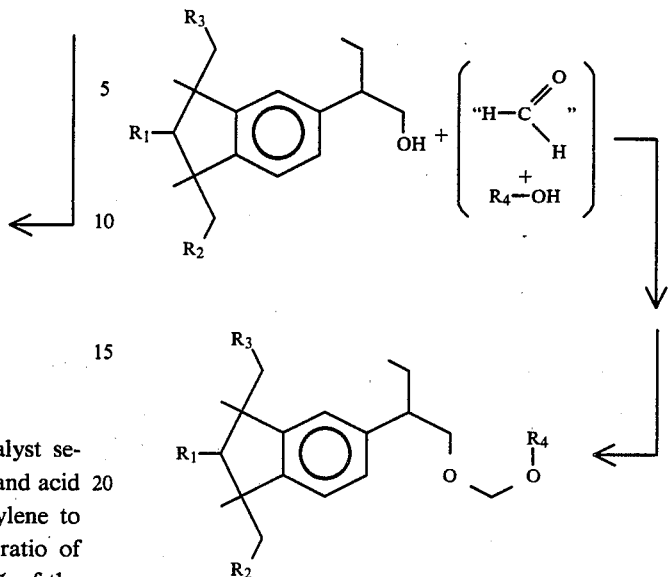

and wherein in the resulting mixture one of $R_1$, $R_2$ and $R_3$ represents methyl and the other of $R_1$, $R_2$ and $R_3$ represent hydrogen; and (iii) reacting the resulting mixture consisting essentially of indane alkanols with formaldehyde or a formaldehyde source in the presence of a lower alkanol according to the reactions:

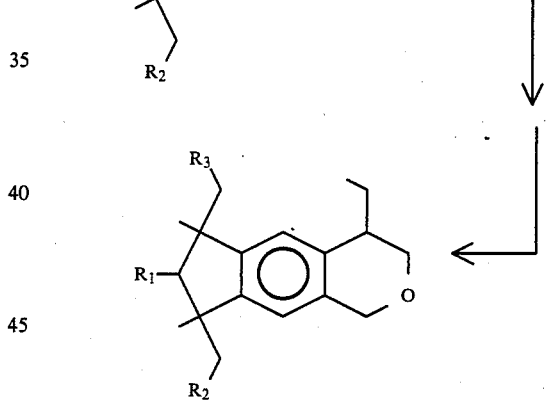

wherein $R_4$ represents $C_1-C_6$ lower alkyl; (iv) subjecting the resulting reaction product to fractional distillation and recovering the fractions boiling at 85°–130° C. at 3.0–5.0 mm/Hg. pressure and having a sweet, musky, caramel aroma.

2. A process for augmenting or enhancing the aroma of a perfume composition, cologne or perfumed article comprising the step of adding to a perfume composition, cologne or perfumed article base an aroma augmenting or enhancing quantity of a product consisting essentially of compounds having the structures:

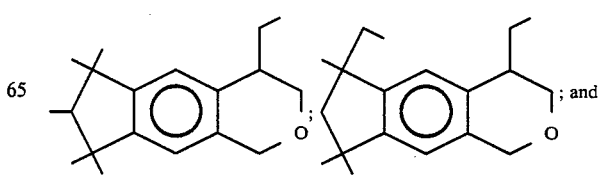

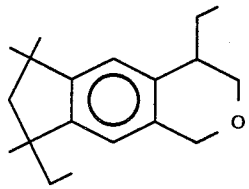

produced according to the process comprising the steps of (i) reacting isoamylene with alpha methyl styrene according to the reaction:

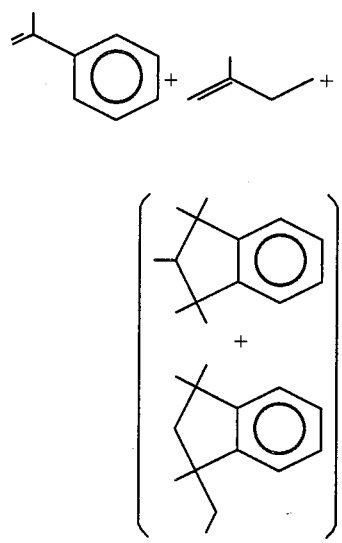

in the presence of a concentrated sulfuric acid catalyst at a temperature in the range of from about 20° C. up to about 50° C. at atmospheric pressure; (ii) reacting the resulting product with 1,2-butylene epoxide in the presence of a catalyst to produce a mixture consisting essentially of indane alkanols according to the reaction:

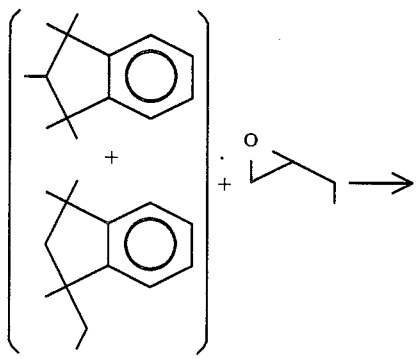

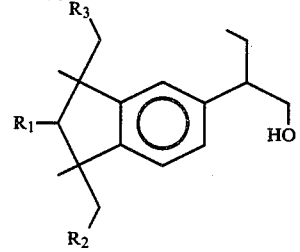

wherein in the resulting mixture one of $R_1$, $R_2$ and $R_3$ represents methyl and the other of $R_1$, $R_2$ and $R_3$ represent hydrogen; and (iii) reacting the resulting mixture consisting essentially of indane alkanols with formaldehyde or formaldehyde source in the presence of a lower alkanol according to the reactions:

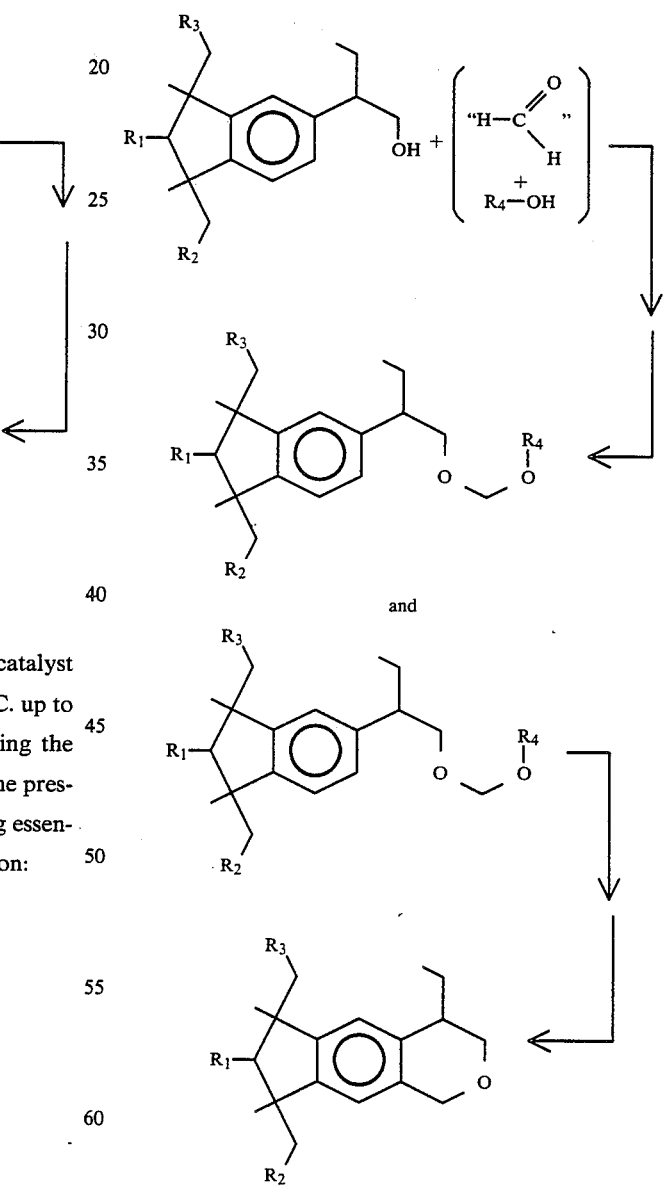

wherein $R_4$ represents $C_1$–$C_6$ lower alkyl; and (iv) subjecting the resulting reaction product to fractional distillation and recovering the fractions boiling at 85°–130° C. at 3.0–5.0 mm/Hg. pressure and having a sweet, musky, caramel aroma.

* * * * *